(12) United States Patent
Forsell

(10) Patent No.: US 8,287,444 B2
(45) Date of Patent: Oct. 16, 2012

(54) MECHANICAL IMPOTENCE TREATMENT APPARATUS

(75) Inventor: Peter Forsell, Bouveret (CH)

(73) Assignee: Obtech Medical AG, Baar (CH)

( * ) Notice: Subject to any disclaimer, the term of this patent is extended or adjusted under 35 U.S.C. 154(b) by 897 days.

(21) Appl. No.: 12/149,207

(22) Filed: Apr. 29, 2008

(65) Prior Publication Data

US 2009/0054725 A1     Feb. 26, 2009

Related U.S. Application Data

(63) Continuation of application No. 10/203,086, filed as application No. PCT/SE01/00271 on Feb. 9, 2001, now Pat. No. 7,367,938.

(60) Provisional application No. 60/181,552, filed on Feb. 10, 2000.

(51) Int. Cl.
*A61F 2/00* (2006.01)

(52) U.S. Cl. .......................................................... 600/37

(58) Field of Classification Search .............. 600/38–41, 600/29–32; 128/DIG. 25
See application file for complete search history.

(56) References Cited

U.S. PATENT DOCUMENTS

| | | |
|---|---|---|
| 2,060,913 A | 11/1936 | Weaver |
| 2,795,641 A | 6/1957 | Rowell |
| 3,209,081 A | 9/1965 | Ducote et al. |
| 3,598,287 A | 8/1971 | De Man |
| 3,662,758 A | 5/1972 | Glover |
| 3,692,027 A | 9/1972 | Ellinwood, Jr. |
| 3,731,679 A | 5/1973 | Wilhelmson et al. |
| 3,731,681 A | 5/1973 | Blackshear et al. |
| 3,750,194 A | 8/1973 | Summers |
| 3,817,237 A | 6/1974 | Bolduc |
| 3,855,122 A | 12/1974 | Bourganel |
| 3,863,622 A * | 2/1975 | Buuck .............................. 600/31 |
| 3,875,928 A | 4/1975 | Angelchik |
| 3,923,060 A | 12/1975 | Ellinwood, Jr. |
| 3,954,102 A | 5/1976 | Buuck |
| 4,003,379 A | 1/1977 | Ellinwood, Jr. |
| 4,009,711 A | 3/1977 | Uson |
| 4,026,305 A | 5/1977 | Brownlee et al. |
| 4,044,401 A | 8/1977 | Guiset |
| 4,201,202 A | 5/1980 | Finney et al. |
| 4,221,219 A | 9/1980 | Tucker |

(Continued)

FOREIGN PATENT DOCUMENTS

DE         2 163 655         3/1986

(Continued)

OTHER PUBLICATIONS

Publication No. EP 1568338A2, dated Aug. 31, 2005, for European Patent Application No. 05010107.0.

(Continued)

*Primary Examiner* — Samuel Gilbert
(74) *Attorney, Agent, or Firm* — Nixon & Vanderhye P.C.

(57) ABSTRACT

A male sexual impotence treatment apparatus comprises an adjustable non-inflatable restriction device (434) implanted in a male impotent patient. The restriction device directly engages a portion of the normal penile tissue of the patient, such as both of the corpora cavernosa as a single unit or one or more of the exit veins from the penis, to affect the blood flow leaving the penis. An adjustment device (436) mechanically adjusts the restriction device to temporarily restrict the blood flow leaving the penis when the patient wishes to achieve erection.

102 Claims, 14 Drawing Sheets

U.S. PATENT DOCUMENTS

| | | |
|---|---|---|
| 4,235,222 A | 11/1980 | Ionescu |
| 4,243,306 A | 1/1981 | Bonini |
| 4,246,893 A | 1/1981 | Berson |
| 4,265,241 A | 5/1981 | Portner et al. |
| 4,271,827 A | 6/1981 | Angelchik |
| 4,274,407 A | 6/1981 | Scarlett |
| 4,304,225 A | 12/1981 | Freeman |
| 4,318,396 A | 3/1982 | Finney |
| 4,342,308 A | 8/1982 | Trick |
| 4,369,771 A | 1/1983 | Trick |
| 4,400,169 A | 8/1983 | Stephens |
| 4,407,278 A | 10/1983 | Burton et al. |
| 4,412,530 A | 11/1983 | Burton |
| 4,424,807 A | 1/1984 | Evans |
| 4,505,710 A | 3/1985 | Collins |
| 4,509,947 A | 4/1985 | Lattin |
| 4,542,753 A | 9/1985 | Brenman et al. |
| 4,550,720 A | 11/1985 | Trick |
| 4,556,050 A | 12/1985 | Hodgson et al. |
| 4,559,930 A | 12/1985 | Cobiski |
| 4,563,175 A | 1/1986 | La Fond |
| 4,583,523 A | 4/1986 | Kleinke et al. |
| 4,584,994 A | 4/1986 | Bamberger et al. |
| 4,592,339 A | 6/1986 | Kuzmak et al. |
| 4,592,355 A | 6/1986 | Antebi |
| 4,599,081 A | 7/1986 | Cohen |
| 4,602,621 A | 7/1986 | Hakky |
| 4,610,658 A | 9/1986 | Buchwald et al. |
| 4,623,350 A | 11/1986 | Lapeyre et al. |
| 4,628,928 A | 12/1986 | Lowell |
| 4,651,721 A | 3/1987 | Mikulich et al. |
| 4,664,100 A | 5/1987 | Rudloff |
| 4,677,534 A | 6/1987 | Okochi |
| 4,679,560 A | 7/1987 | Galbraith |
| 4,696,288 A | 9/1987 | Kuzmak et al. |
| 4,699,128 A | 10/1987 | Hemmeter |
| 4,711,231 A | 12/1987 | Finegold et al. |
| 4,723,538 A | 2/1988 | Stewart et al. |
| 4,756,949 A | 7/1988 | Spence et al. |
| 4,771,780 A | 9/1988 | Sholder |
| 4,828,544 A | 5/1989 | Lane et al. |
| 4,828,990 A | 5/1989 | Higashi et al. |
| 4,829,990 A | 5/1989 | Thuroff et al. |
| 4,846,794 A | 7/1989 | Hertzer |
| 4,902,279 A | 2/1990 | Schmidtz et al. |
| 4,925,443 A | 5/1990 | Heilman et al. |
| 4,941,461 A | 7/1990 | Fischell |
| 4,942,668 A | 7/1990 | Franklin |
| 4,958,630 A | 9/1990 | Rosenbluth et al. |
| 4,979,955 A | 12/1990 | Smith |
| 4,982,731 A | 1/1991 | Lue et al. |
| 4,983,177 A | 1/1991 | Wolf |
| 5,006,106 A | 4/1991 | Angelchik |
| 5,012,822 A | 5/1991 | Schwarz |
| 5,042,084 A | 8/1991 | Daly |
| 5,048,511 A | 9/1991 | Rosenbluth et al. |
| 5,057,075 A | 10/1991 | Moncrief et al. |
| 5,062,416 A | 11/1991 | Stucks |
| 5,074,868 A | 12/1991 | Kuzmak |
| 5,088,477 A | 2/1992 | Subrini |
| 5,098,369 A | 3/1992 | Heilman et al. |
| 5,112,202 A | 5/1992 | Oshima et al. |
| 5,112,295 A | 5/1992 | Zinner et al. |
| 5,123,428 A | 6/1992 | Schwarz |
| 5,160,338 A | 11/1992 | Vincent |
| 5,167,611 A | 12/1992 | Cowan |
| 5,226,429 A | 7/1993 | Kuzmak |
| 5,250,020 A | 10/1993 | Bley |
| 5,297,536 A | 3/1994 | Wilk |
| 5,304,206 A | 4/1994 | Baker, Jr. et al. |
| 5,316,543 A | 5/1994 | Eberbach |
| 5,358,474 A | 10/1994 | Kaldany |
| 5,415,660 A | 5/1995 | Campbell et al. |
| 5,437,605 A | 8/1995 | Helmy |
| 5,449,368 A | 9/1995 | Kuzmak |
| 5,453,079 A | 9/1995 | Schwaninger |
| 5,454,840 A | 10/1995 | Krakovsky et al. |
| 5,501,703 A | 3/1996 | Holsheimer et al. |
| 5,505,733 A | 4/1996 | Justin et al. |
| 5,509,888 A | 4/1996 | Miller |
| 5,518,504 A | 5/1996 | Polyak |
| 5,540,731 A | 7/1996 | Testerman |
| 5,569,187 A | 10/1996 | Kaiser |
| 5,578,069 A | 11/1996 | Miner, II |
| 5,582,580 A | 12/1996 | Buckman, Jr. et al. |
| 5,665,065 A | 9/1997 | Colman et al. |
| 5,676,674 A | 10/1997 | Bolanos et al. |
| 5,690,108 A | 11/1997 | Chakeres |
| 5,702,431 A | 12/1997 | Wang et al. |
| 5,704,893 A | 1/1998 | Timm |
| 5,735,887 A | 4/1998 | Barreras et al. |
| 5,749,909 A | 5/1998 | Schroppel et al. |
| 5,769,877 A | 6/1998 | Barreras |
| 5,771,903 A | 6/1998 | Jakobsson |
| 5,814,020 A | 9/1998 | Gross |
| 5,823,991 A | 10/1998 | Shim |
| 5,827,286 A | 10/1998 | Incavo et al. |
| 5,848,962 A | 12/1998 | Feindt et al. |
| 5,858,001 A | 1/1999 | Tsals et al. |
| 5,876,425 A | 3/1999 | Gord et al. |
| 5,899,849 A | 5/1999 | Elist |
| 5,900,909 A | 5/1999 | Parulski et al. |
| 5,902,336 A | 5/1999 | Mishkin |
| 5,910,149 A | 6/1999 | Kuzmak |
| 5,928,195 A | 7/1999 | Malamud et al. |
| 5,938,584 A | 8/1999 | Ardito et al. |
| 5,938,669 A | 8/1999 | Klaiber et al. |
| 5,954,715 A | 9/1999 | Harrington et al. |
| 5,964,789 A | 10/1999 | Karsdon |
| 5,978,712 A | 11/1999 | Suda et al. |
| 5,995,874 A | 11/1999 | Borza |
| 5,997,501 A | 12/1999 | Gross et al. |
| 6,003,736 A | 12/1999 | Ljunggren |
| 6,067,991 A | 5/2000 | Forsell |
| 6,074,341 A | 6/2000 | Anderson et al. |
| 6,077,215 A | 6/2000 | Leysieffer |
| 6,095,968 A | 8/2000 | Snyders |
| 6,102,887 A | 8/2000 | Altman |
| 6,102,922 A | 8/2000 | Jakobsson et al. |
| 6,113,574 A | 9/2000 | Spinello |
| 6,116,193 A | 9/2000 | Goeckner |
| 6,117,067 A | 9/2000 | Gil-Vernet |
| 6,134,470 A | 10/2000 | Hartlaub |
| 6,135,945 A | 10/2000 | Sultan |
| 6,162,238 A | 12/2000 | Kaplan et al. |
| 6,185,452 B1 | 2/2001 | Schulman et al. |
| 6,197,055 B1 | 3/2001 | Matthews |
| 6,210,347 B1 | 4/2001 | Forsell |
| 6,221,060 B1 | 4/2001 | Willard |
| 6,233,474 B1 | 5/2001 | Lemelsom |
| 6,275,737 B1 | 8/2001 | Mann |
| 6,319,191 B1 | 11/2001 | Sayet et al. |
| 6,332,466 B1 | 12/2001 | Yoon |
| 6,346,099 B1 | 2/2002 | Altman |
| 6,436,054 B1 | 8/2002 | Viola et al. |
| 6,450,173 B1 | 9/2002 | Forsell |
| 6,450,946 B1 | 9/2002 | Forsell |
| 6,453,907 B1 | 9/2002 | Forsell |
| 6,454,698 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |
| 6,456,883 B1 | 9/2002 | Torgerson et al. |
| 6,460,543 B1 | 10/2002 | Forsell |
| 6,461,292 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,470,892 B1 | 10/2002 | Forsell |
| 6,471,635 B1 | 10/2002 | Forsell |
| 6,475,136 B1 | 11/2002 | Forsell |
| 6,475,137 B1 | 11/2002 | Elist |
| 6,482,145 B1 | 11/2002 | Forsell |
| 6,503,189 B1 | 1/2003 | Forsell |
| 6,571,127 B1 | 5/2003 | Ben-Haim et al. |
| 6,572,585 B2 | 6/2003 | Choi |
| 6,589,229 B1 | 7/2003 | Connelly et al. |

| | | |
|---|---|---|
| 6,638,208 B1 | 10/2003 | Natarajan et al. |
| 6,638,303 B1 | 10/2003 | Campbell |
| 6,659,936 B1 | 12/2003 | Furness et al. |
| 6,678,561 B2 | 1/2004 | Forsell |
| 6,689,085 B1 | 2/2004 | Rubenstein et al. |
| 6,709,385 B2 | 3/2004 | Forsell |
| 6,740,075 B2 | 5/2004 | Lebel et al. |
| 6,772,011 B2 | 8/2004 | Dolgin |
| 6,895,280 B2 | 5/2005 | Meadows et al. |
| 6,911,002 B2 | 6/2005 | Fierro |
| 6,915,165 B2 | 7/2005 | Forsell |
| 6,948,918 B2 | 9/2005 | Hansen |
| 6,953,429 B2 | 10/2005 | Forsell |
| 6,960,233 B1 | 11/2005 | Berg et al. |
| 7,011,624 B2 | 3/2006 | Forsell |
| 7,017,583 B2 | 3/2006 | Forsell |
| 7,043,295 B2 | 5/2006 | Starkebaum |
| 7,066,922 B2 | 6/2006 | Angel et al. |
| 7,108,686 B2 | 9/2006 | Burke et al. |
| 7,207,936 B2 | 4/2007 | Forsell |
| 7,235,044 B2 | 6/2007 | Forsell |
| 7,238,165 B2 | 7/2007 | Vincent |
| 7,250,037 B2 | 7/2007 | Shermer et al. |
| 7,311,690 B2 | 12/2007 | Burnett |
| 7,338,437 B2 | 3/2008 | Forsell |
| 7,367,938 B2 | 5/2008 | Forsell |
| 7,371,208 B2 | 5/2008 | Forsell |
| 7,390,296 B2 | 6/2008 | Mische |
| 7,395,822 B1 | 7/2008 | Burton et al. |
| 7,407,479 B2 | 8/2008 | Forsell |
| 7,407,481 B2 | 8/2008 | Forsell |
| 7,442,165 B2 | 10/2008 | Forsell |
| 7,455,663 B2 | 11/2008 | Bikovsky |
| 7,569,050 B2 | 8/2009 | Moberg et al. |
| 7,621,863 B2 | 11/2009 | Forsell |
| 7,648,455 B2 | 1/2010 | Forsell |
| 7,666,132 B2 | 2/2010 | Forsell |
| 7,669,601 B2 | 3/2010 | Tal |
| 7,846,160 B2 | 12/2010 | Payne et al. |
| 7,972,354 B2 | 7/2011 | Prestezog et al. |
| 7,987,853 B2 | 8/2011 | Swann et al. |
| 2001/0011543 A1 | 8/2001 | Forsell |
| 2001/0016738 A1 | 8/2001 | Harrington et al. |
| 2002/0022759 A1 | 2/2002 | Forsell |
| 2002/0028980 A1 | 3/2002 | Thierfelder et al. |
| 2002/0040208 A1 | 4/2002 | Flaherty et al. |
| 2002/0055711 A1 | 5/2002 | Lavi et al. |
| 2002/0072759 A1 | 6/2002 | Fry |
| 2002/0095139 A1 | 7/2002 | Keogh et al. |
| 2002/0095164 A1 | 7/2002 | Andreas et al. |
| 2002/0151922 A1 | 10/2002 | Hogendijk et al. |
| 2002/0165575 A1 | 11/2002 | Saleh |
| 2002/0183588 A1 | 12/2002 | Fierro |
| 2003/0009221 A1 | 1/2003 | Forsell |
| 2003/0014010 A1 | 1/2003 | Carpenter et al. |
| 2003/0014086 A1 | 1/2003 | Sharma |
| 2003/0021822 A1 | 1/2003 | Lloyd |
| 2003/0032855 A1 | 2/2003 | Shahinpoor |
| 2003/0032857 A1 | 2/2003 | Forsell |
| 2003/0050591 A1 | 3/2003 | Patrick McHale |
| 2003/0055442 A1 | 3/2003 | Laufer et al. |
| 2003/0060893 A1 | 3/2003 | Forsell |
| 2003/0066536 A1 | 4/2003 | Forsell |
| 2003/0069547 A1 | 4/2003 | Gonon |
| 2003/0088148 A1 | 5/2003 | Forsell |
| 2003/0092962 A1 | 5/2003 | Forsell |
| 2003/0100929 A1 | 5/2003 | Forsell |
| 2003/0105385 A1 | 6/2003 | Forsell |
| 2003/0109771 A1 | 6/2003 | Forsell |
| 2003/0125605 A1 | 7/2003 | Forsell |
| 2003/0125768 A1 | 7/2003 | Peter |
| 2003/0144648 A1 | 7/2003 | Forsell |
| 2003/0163029 A1 | 8/2003 | Sonnenschein et al. |
| 2003/0208247 A1 | 11/2003 | Spinelli et al. |
| 2003/0233143 A1 | 12/2003 | Gharib et al. |
| 2004/0024419 A1 | 2/2004 | Slepian et al. |
| 2004/0034275 A1 | 2/2004 | Forsell |
| 2004/0068299 A1 | 4/2004 | Laske et al. |
| 2004/0089313 A1 | 5/2004 | Utley et al. |
| 2004/0102804 A1 | 5/2004 | Chin |
| 2004/0122526 A1 | 6/2004 | Imran |
| 2004/0122527 A1 | 6/2004 | Imran |
| 2004/0147871 A1 | 7/2004 | Burnett |
| 2004/0162568 A1 | 8/2004 | Saadat et al. |
| 2004/0177918 A1 | 9/2004 | Murata et al. |
| 2004/0249451 A1 | 12/2004 | Lu et al. |
| 2004/0260316 A1 | 12/2004 | Knudson et al. |
| 2005/0038484 A1 | 2/2005 | Knudson et al. |
| 2005/0055025 A1 | 3/2005 | Zacouto et al. |
| 2005/0075697 A1 | 4/2005 | Olson et al. |
| 2005/0209633 A1 | 9/2005 | Callister et al. |
| 2005/0240229 A1 | 10/2005 | Whitehurst et al. |
| 2005/0245957 A1 | 11/2005 | Starkebaum et al. |
| 2005/0261712 A1 | 11/2005 | Balbierz et al. |
| 2005/0266042 A1 | 12/2005 | Tseng |
| 2005/0267405 A1 | 12/2005 | Shah |
| 2005/0267596 A1 | 12/2005 | Chen et al. |
| 2006/0069414 A1 | 3/2006 | Imran et al. |
| 2006/0127246 A1 | 6/2006 | Forsell |
| 2006/0142635 A1 | 6/2006 | Forsell |
| 2006/0149124 A1 | 7/2006 | Forsell |
| 2006/0149129 A1 | 7/2006 | Watts et al. |
| 2006/0167539 A1 | 7/2006 | Mcewan |
| 2006/0212055 A1 | 9/2006 | Karabey et al. |
| 2006/0224177 A1 | 10/2006 | Finitsis |
| 2006/0229688 A1 | 10/2006 | McClure et al. |
| 2006/0235482 A1 | 10/2006 | Forsell |
| 2006/0257446 A1 | 11/2006 | Tropsha et al. |
| 2007/0015959 A1 | 1/2007 | Forsell |
| 2007/0038232 A1 | 2/2007 | Kraemer |
| 2007/0049790 A1 | 3/2007 | Wagner et al. |
| 2007/0073099 A1 | 3/2007 | Forsell |
| 2007/0092862 A1 | 4/2007 | Gerber |
| 2007/0156204 A1 | 7/2007 | Denker et al. |
| 2007/0167670 A1 | 7/2007 | Coleman et al. |
| 2007/0193632 A1 | 8/2007 | Shu |
| 2007/0225802 A1 | 9/2007 | Forsell |
| 2007/0232848 A1 | 10/2007 | Forsell |
| 2007/0233019 A1 | 10/2007 | Forsell |
| 2007/0250020 A1 | 10/2007 | Kim et al. |
| 2007/0265675 A1 | 11/2007 | Lund et al. |
| 2008/0004487 A1 | 1/2008 | Haverfield |
| 2008/0045783 A1 | 2/2008 | Forsell |
| 2008/0051718 A1 | 2/2008 | Kavazov et al. |
| 2008/0086179 A1 | 4/2008 | Sharma |
| 2008/0103544 A1 | 5/2008 | Weiner |
| 2008/0154256 A1 | 6/2008 | Payne et al. |
| 2008/0178889 A1 | 7/2008 | Tal |
| 2008/0200753 A1 | 8/2008 | Forsell |
| 2008/0214888 A1 | 9/2008 | Shalom |
| 2008/0245371 A1 | 10/2008 | Gruber |
| 2008/0269548 A1 | 10/2008 | Vecchiotti et al. |
| 2008/0275296 A1 | 11/2008 | Forsell |
| 2009/0018388 A1 | 1/2009 | Forsell |
| 2009/0024108 A1 | 1/2009 | Lee-Sepsick et al. |
| 2009/0054725 A1 | 2/2009 | Forsell |
| 2009/0131959 A1 | 5/2009 | Rolland |
| 2009/0240100 A1 | 9/2009 | Forsell |
| 2009/0240294 A1 | 9/2009 | Forsell |
| 2009/0247817 A1 | 10/2009 | Forsell |
| 2009/0247818 A1 | 10/2009 | Forsell |
| 2009/0248033 A1 | 10/2009 | Forsell |
| 2009/0250068 A1 | 10/2009 | Forsell |
| 2009/0254106 A1 | 10/2009 | Forsell |
| 2009/0266366 A1 | 10/2009 | Swann et al. |
| 2010/0145138 A1 | 6/2010 | Forsell |
| 2010/0145139 A1 | 6/2010 | Forsell |
| 2010/0217067 A1 | 8/2010 | Forsell |
| 2010/0286735 A1 | 11/2010 | Garfield et al. |
| 2010/0312047 A1 | 12/2010 | Forsell |
| 2010/0312048 A1 | 12/2010 | Forsell |
| 2010/0312049 A1 | 12/2010 | Forsell |
| 2010/0312050 A1 | 12/2010 | Forsell |
| 2010/0312163 A1 | 12/2010 | Forsell |
| 2010/0312164 A1 | 12/2010 | Forsell |
| 2010/0312356 A1 | 12/2010 | Forsell |
| 2010/0318116 A1 | 12/2010 | Forsell |
| 2010/0318117 A1 | 12/2010 | Forsell |

| | | | |
|---|---|---|---|
| 2010/0318118 A1 | 12/2010 | Forsell | |
| 2010/0324360 A1 | 12/2010 | Forsell | |
| 2010/0324361 A1 | 12/2010 | Forsell | |
| 2010/0324362 A1 | 12/2010 | Forsell | |
| 2010/0324591 A1 | 12/2010 | Forsell | |
| 2010/0331614 A1 | 12/2010 | Forsell | |
| 2010/0331615 A1 | 12/2010 | Forsell | |
| 2010/0331616 A1 | 12/2010 | Forsell | |
| 2010/0331617 A1 | 12/2010 | Forsell | |
| 2010/0331945 A1 | 12/2010 | Forsell | |
| 2010/0332000 A1 | 12/2010 | Forsell | |
| 2011/0009894 A1 | 1/2011 | Forsell | |
| 2011/0009896 A1 | 1/2011 | Forsell | |
| 2011/0009897 A1 | 1/2011 | Forsell | |
| 2011/0015473 A1 | 1/2011 | Forsell | |
| 2011/0015474 A1 | 1/2011 | Forsell | |
| 2011/0022323 A1 | 1/2011 | Yundt-Pacheco et al. | |
| 2011/0022324 A1 | 1/2011 | Knopp et al. | |
| 2011/0040143 A1 | 2/2011 | Forsell | |
| 2011/0172693 A1 | 7/2011 | Forsell | |
| 2011/0184230 A1 | 7/2011 | Forsell | |
| 2011/0192402 A1 | 8/2011 | Forsell | |
| 2011/0196192 A1 | 8/2011 | Forsell | |
| 2011/0196193 A1 | 8/2011 | Forsell | |
| 2011/0196194 A1 | 8/2011 | Forsell | |
| 2011/0196271 A1 | 8/2011 | Forsell | |
| 2011/0196371 A1 | 8/2011 | Forsell | |
| 2011/0196391 A1 | 8/2011 | Forsell | |
| 2011/0196411 A1 | 8/2011 | Forsell | |
| 2011/0196435 A1 | 8/2011 | Forsell | |
| 2011/0196466 A1 | 8/2011 | Forsell | |
| 2011/0196476 A1 | 8/2011 | Forsell | |
| 2011/0196481 A1 | 8/2011 | Forsell | |
| 2011/0196482 A1 | 8/2011 | Forsell | |
| 2011/0196483 A1 | 8/2011 | Forsell | |
| 2011/0196484 A1 | 8/2011 | Forsell | |
| 2011/0196485 A1 | 8/2011 | Forsell | |
| 2011/0196486 A1 | 8/2011 | Forsell | |
| 2011/0196505 A1 | 8/2011 | Forsell | |
| 2011/0196506 A1 | 8/2011 | Forsell | |
| 2011/0201870 A1 | 8/2011 | Forsell | |
| 2011/0201871 A1 | 8/2011 | Forsell | |
| 2011/0201873 A1 | 8/2011 | Forsell | |
| 2011/0202041 A1 | 8/2011 | Forsell | |
| 2011/0202129 A1 | 8/2011 | Fofsell | |
| 2011/0202131 A1 | 8/2011 | Forsell | |
| 2011/0208231 A1 | 8/2011 | Forsell | |
| 2011/0218394 A1 | 9/2011 | Forsell | |
| 2011/0224787 A1 | 9/2011 | Forsell | |
| 2011/0230930 A1 | 9/2011 | Forsell | |
| 2011/0263928 A1 | 10/2011 | Forsell | |

FOREIGN PATENT DOCUMENTS

| | | |
|---|---|---|
| DE | 19511998 | 10/1996 |
| DE | 199 03 246 | 8/2000 |
| EP | 0102548 | 3/1984 |
| EP | 01 343 40 | 3/1985 |
| EP | 0 200 286 | 11/1986 |
| EP | 0300552 | 1/1989 |
| EP | 0378251 | 7/1990 |
| EP | 0412191 | 2/1991 |
| EP | 0 583 012 | 2/1994 |
| EP | 0611561 | 9/1994 |
| EP | 0876808 | 11/1998 |
| EP | 1 004 330 | 5/2000 |
| EP | 1 033 142 | 9/2000 |
| EP | 1 072 238 | 1/2001 |
| EP | 1 514 526 | 3/2005 |
| EP | 1563814 | 8/2005 |
| EP | 1563886 | 8/2005 |
| EP | 1 586 283 | 10/2005 |
| EP | 1598030 | 11/2005 |
| EP | 1 681 041 | 7/2006 |
| EP | 1 878 452 | 1/2008 |
| EP | 1 913 880 | 4/2008 |
| FR | 2688693 | 9/1993 |
| FR | 2692777 | 12/1993 |
| FR | 27565485 | 6/1998 |
| FR | 2797181 | 2/2001 |
| GB | 8 856 74 | 12/1961 |
| GB | 1194358 | 6/1970 |
| WO | WO 84/01282 | 4/1984 |
| WO | WO 94/27504 | 12/1994 |
| WO | 96/01597 | 1/1996 |
| WO | WO 96/01597 | 1/1996 |
| WO | WO 96/11036 | 4/1996 |
| WO | WO 96/39932 | 12/1996 |
| WO | 97/41799 | 11/1997 |
| WO | WO 97/41799 | 11/1997 |
| WO | WO 98/50099 | 11/1998 |
| WO | WO 99/18885 | 4/1999 |
| WO | WO 00/09048 | 2/2000 |
| WO | WO 00/15158 | 3/2000 |
| WO | WO 00/16686 | 3/2000 |
| WO | WO 01/12078 | 2/2001 |
| WO | WO 01/12108 | 2/2001 |
| WO | WO 01/45487 | 6/2001 |
| WO | WO 01/45590 | 6/2001 |
| WO | WO 01/47575 | 7/2001 |
| WO | WO 0147434 | 7/2001 |
| WO | WO 0147439 | 7/2001 |
| WO | WO 01/58391 | 8/2001 |
| WO | WO 0154615 | 8/2001 |
| WO | WO 01/67964 | 9/2001 |
| WO | WO 02/38217 | 5/2002 |
| WO | WO 02/40083 | 5/2002 |
| WO | WO 02/053210 | 7/2002 |
| WO | WO 02/058563 | 8/2002 |
| WO | WO 02/087657 | 11/2002 |
| WO | WO 02/100481 | 12/2002 |
| WO | WO 03/002192 | 1/2003 |
| WO | WO 03/033054 | 4/2003 |
| WO | WO 2004/012806 | 2/2004 |
| WO | WO 2004/018037 | 3/2004 |
| WO | WO 2004/019765 | 3/2004 |
| WO | WO 2004/060171 | 7/2004 |
| WO | WO 2004/071684 | 8/2004 |
| WO | WO 2004/101029 | 11/2004 |
| WO | WO 98/06358 | 2/2005 |
| WO | WO 2005/072169 | 8/2005 |
| WO | WO 2005/105003 | 11/2005 |
| WO | WO 2006/114004 | 11/2006 |
| WO | WO 2006/122285 | 11/2006 |
| WO | WO 2006/134106 | 12/2006 |
| WO | WO 2007/017880 | 2/2007 |
| WO | WO 2007/041795 | 4/2007 |
| WO | WO 0147435 | 4/2007 |
| WO | WO 2007/051563 | 5/2007 |
| WO | WO 2007/109759 | 9/2007 |
| WO | WO 2007/137026 | 11/2007 |
| WO | WO 2007/149555 | 12/2007 |
| WO | WO 2008/135988 | 11/2008 |
| WO | WO 2009/010799 | 1/2009 |
| WO | WO 2009/096854 | 8/2009 |
| WO | WO 2009/096865 | 8/2009 |
| WO | WO 2009/096868 | 8/2009 |
| WO | WO 2009/115645 | 9/2009 |

OTHER PUBLICATIONS

European Search Report, dated Sep. 14, 2006, for EP 05010107.0.
Examination Report, dated Nov. 4, 2008, in European Patent Application No. 05010107.0.
Webster's II New River side University, 1984, pp. 573,1000.
European Search Report for EP 05 010 084 dated Jun. 27, 2005.
European Examination Report for EP 05 010 046.0 dated May 19, 2006 (4 pages).
International Search Report for International Application No. PCT/SE01/00271, "2001".
U.S. Appl. No. 09/373,224, Forsell, filed Aug. 12, 1999.
U.S. Appl. No. 11/988, 450, Forsell, filed May 27, 2009.
Anand, Sneh. "Electrical Pacing of the Ampullary Isthmic Junction for Contraception",IEEE Engineering in Medicine & Biology 10TH Annual International Conference, 1988.
International Search Report for PCT/SE2010/050091, Mailed May 6, 2010.
International Search Report for PCT/SE2010/050092, Mailed May 6, 2010.

* cited by examiner

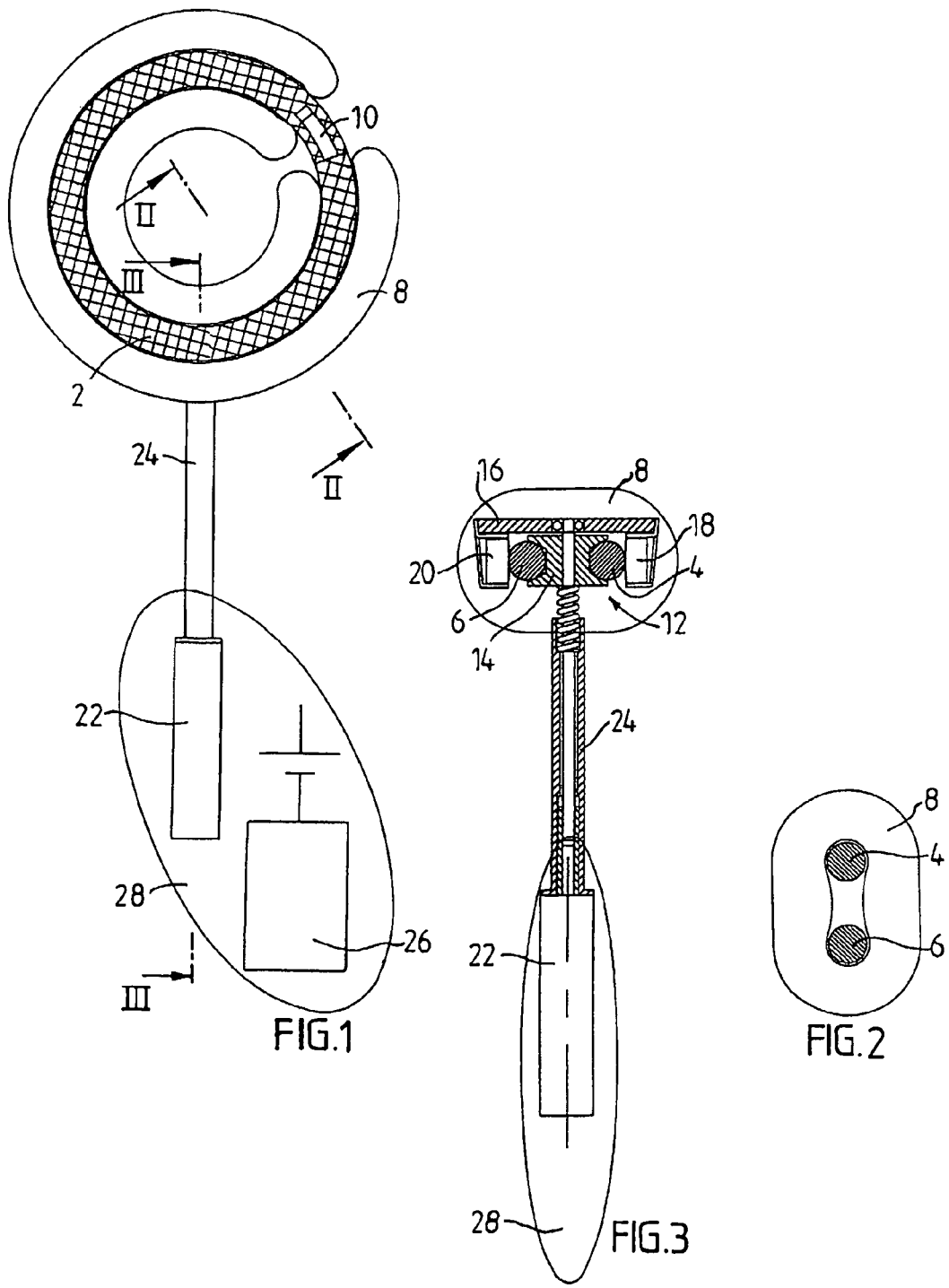

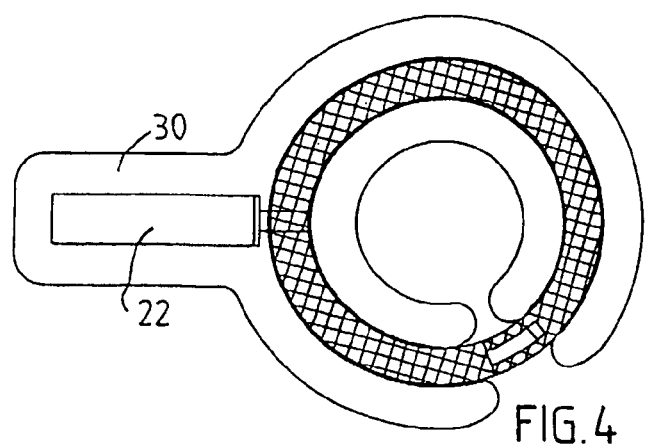
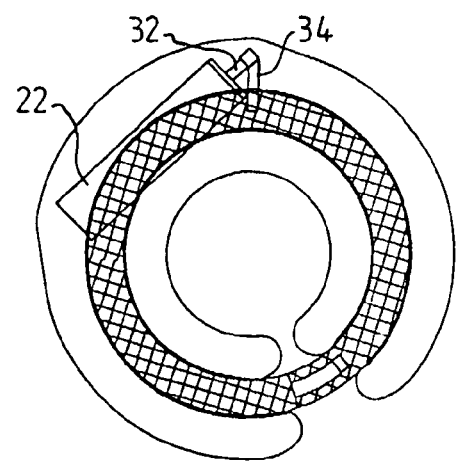
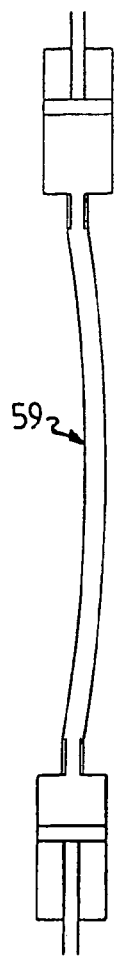
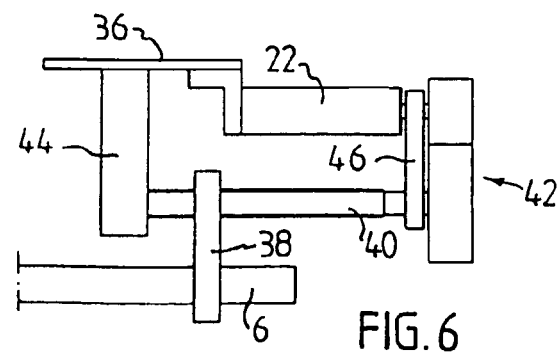

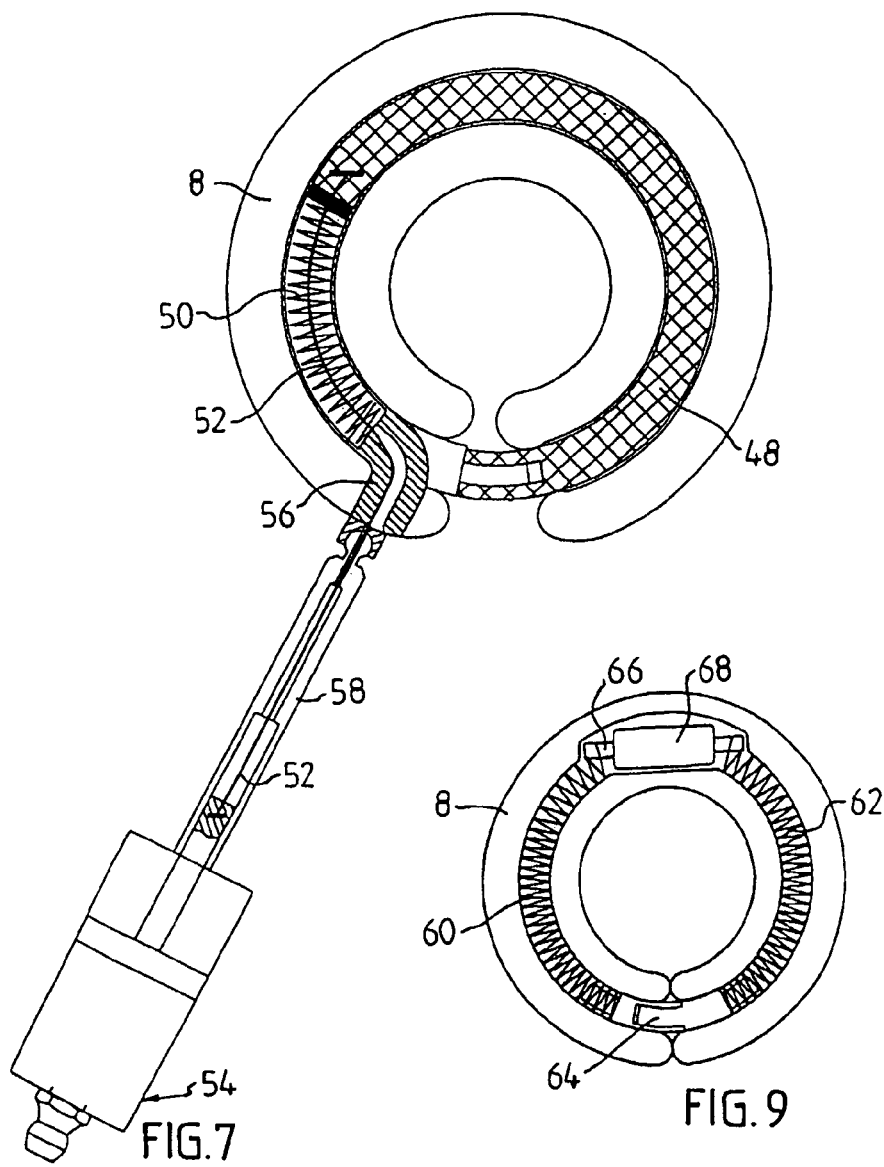
FIG. 7
FIG. 9
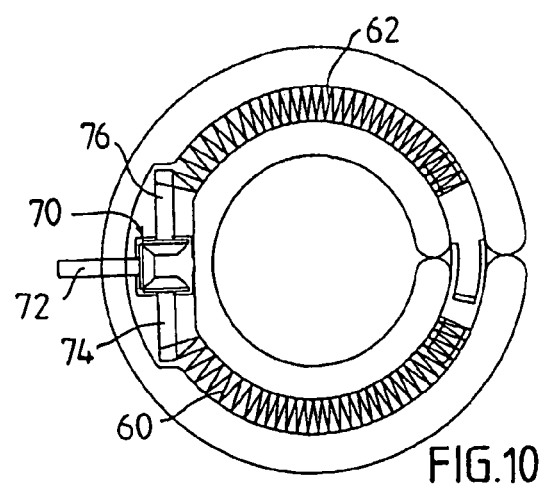
FIG. 10

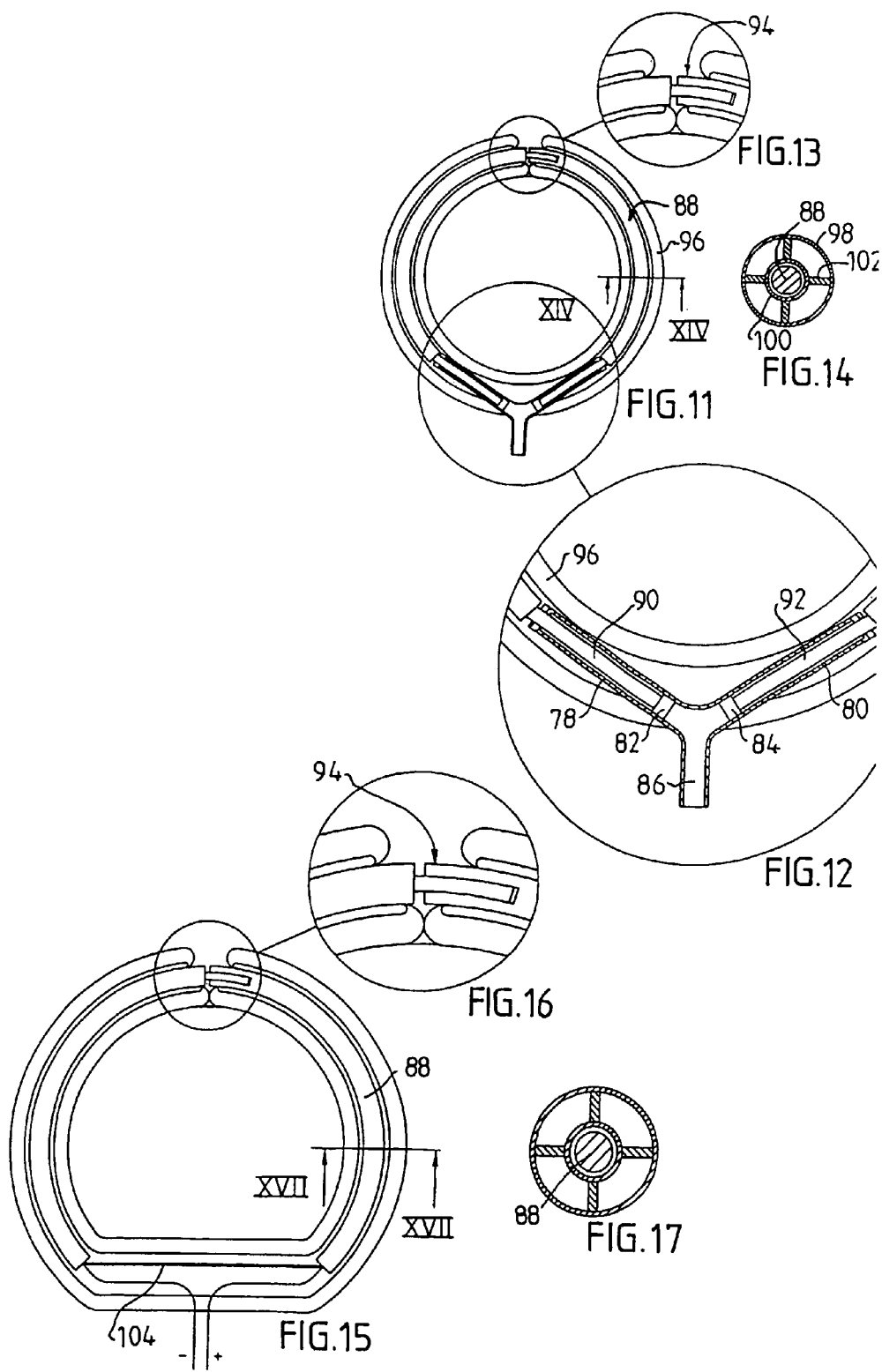

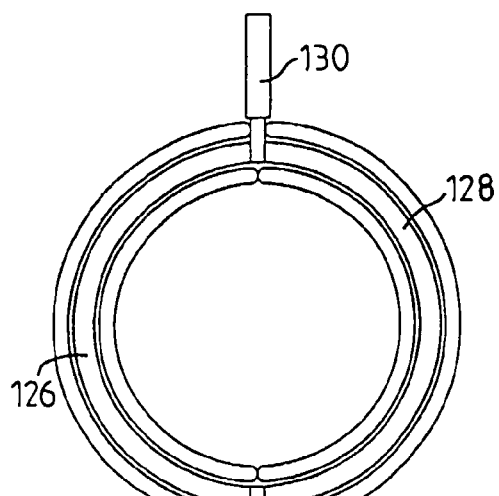
FIG. 21
FIG. 22
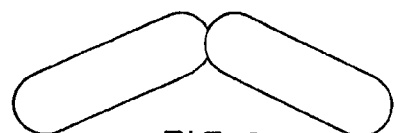
FIG. 23
A-A
A-A
FIG. 26
FIG. 27
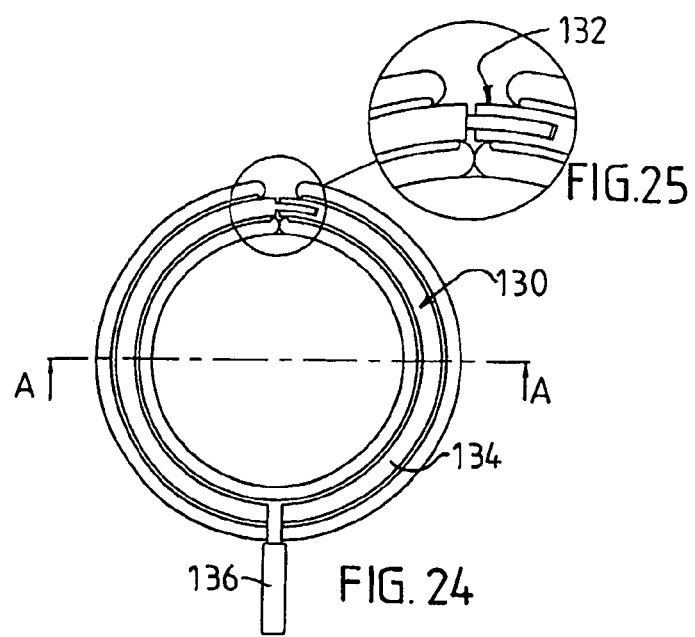
FIG. 25
FIG. 24

NO FLOW

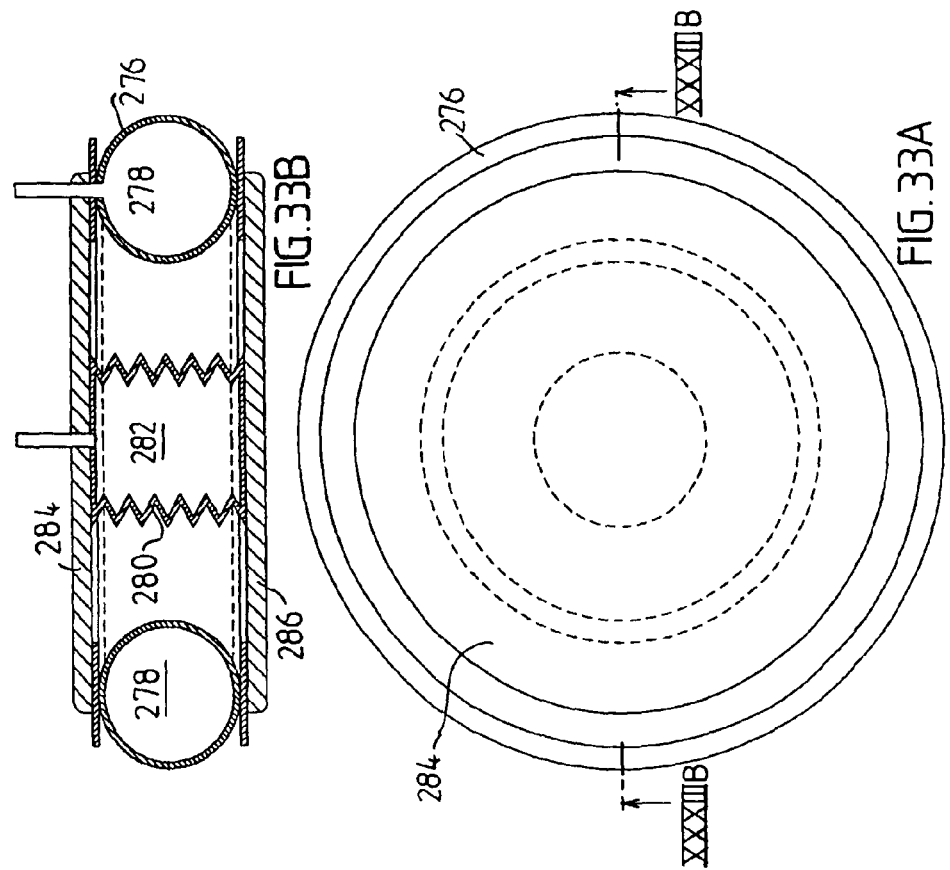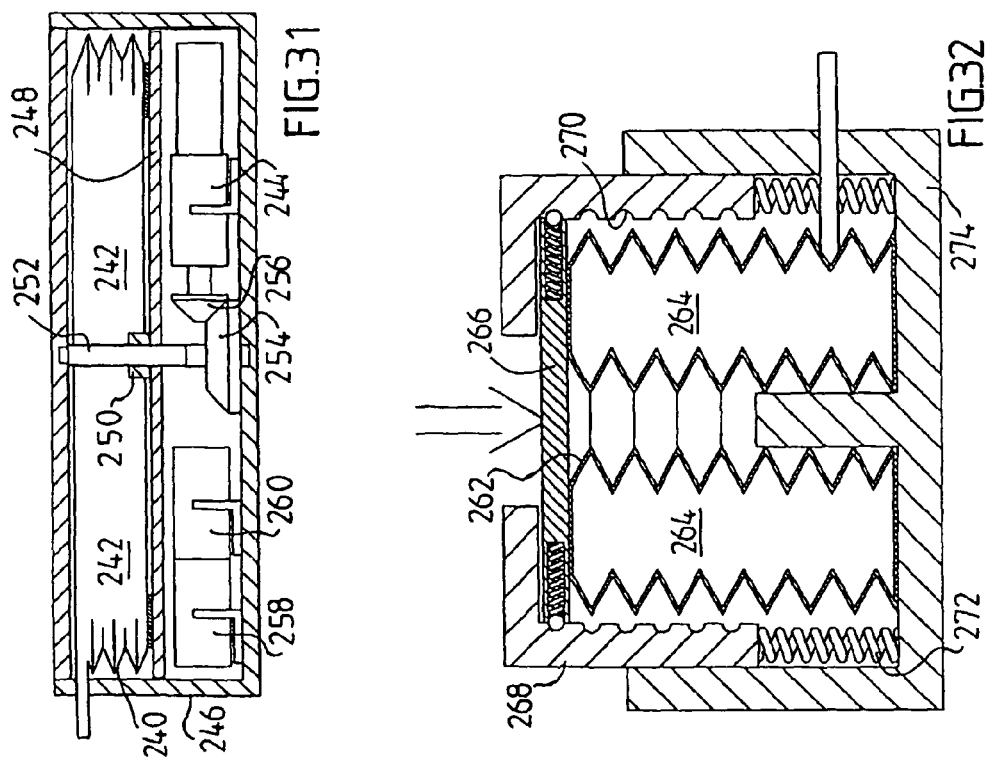

MECHANICAL IMPOTENCE TREATMENT APPARATUS

This application is a continuation of U.S. application Ser. No. 10/203,086, filed Oct. 24, 2002 now U.S. Pat. No. 7,367,938, now allowed, which is the U.S. National Phase of International Application PCT/SE01/00271, filed Feb. 9, 2001, which designated the U.S., which claims the benefit of U.S. Provisional Application No. 60/181,552, filed Feb. 10, 2000, the entire contents of which are hereby incorporated by reference in this application.

The present invention relates to a male sexual impotence treatment apparatus, comprising an adjustable restriction device implantable in a male patient, who suffers from sexual impotence, for directly engaging a portion of the normal penile tissue or the prolongation thereof of the patient, and an operable adjustment device implantable in the patient for adjusting the restriction device to temporarily contract said portion of the normal penile tissue or the prolongation thereof to restrict the blood flow leaving the penis, when the patient desires to achieve erection.

Male sexual impotence is a widespread problem. Many different solutions to this problem have been tried. A main solution currently practised and disclosed in for instance U.S. Pat. Nos. 5,437,605 and 4,841,461 is to implant a hydraulic inflatable/contractible silicon prosthesis in the cavities of the corpora cavernosa of the patient's penis. In fluid connection with this prosthesis is a reservoir implanted in the scrotum. By manual pumping action the prosthesis is filled with fluid from the reservoir to effect erect condition or is emptied of fluid, which returns to the reservoir, to effect flaccid condition.

However, there are several more or less severe disadvantages of this main solution. Above all, the penis is more or less damaged by the operation and it is practically impossible to reverse the operation. Another disadvantage is that rather strong forces act against this implanted prosthesis resulting in a significant risk of the prosthesis being broken. A further disadvantage is that hard fibrosis created around the reservoir over time may cause malfunction of pumping components. Thus, the created fibrosis will sooner or later become a hard fibrotic layer which may make it difficult to pump the reservoir. Yet a further disadvantage is that the use of hydraulic fluid always entails a risk of fluid leaking from the prosthesis. Furthermore, it is a rather complicated task to manually pump the reservoir when erection is desired.

Another solution to achieve erection is to restrict the blood flow leaving the penis. For example, U.S. Pat. No. 4,829,990 discloses two hydraulically operated inflatable cuffs wrapped around the respective crura. Again, a disadvantage of such a solution is that it entails a risk of hydraulic fluid leaking from the cuffs.

Another example of the solution to restrict the penile blood flow is found in U.S. Pat. No. 4,828,544, which discloses an artificial fistula system surgically implanted and providing a primary fistula between the femoral artery and the femoral vein and a secondary fistula for leading blood from the primary fistula to the penis. An inflatable balloon engages the primary fistula between the secondary fistula and the vein. The balloon is in fluid connection with a manually compressible reservoir implanted in the scrotum. Besides the risk of fluid leaking from the balloon, a further disadvantage of this latter example is that it requires delicate surgery.

A main disadvantage of the solution to restrict the penile blood flow is the fact that the venous blood vessel system is rather complex and it is difficult to restrict the veinplexa.

Yet another solution is to inject a substance in the vein system to achieve erection. However, injections are painful and complicated for the patient.

The prime object of the present invention is to provide a male sexual impotence treatment apparatus in which the risk of liquid leaking from implanted hydraulic components of the apparatus is substantially reduced or completely eliminated.

A further object of the invention is to provide a male sexual impotence treatment apparatus, which does not require surgical implantation of any fistula system.

Another object of the invention is to provide a male sexual impotence treatment apparatus, which does not require the use of an injection needle.

These objects are obtained by an apparatus of the kind stated initially, which is characterised in that the adjustment device is adapted to mechanically adjust the restriction device.

The restriction device preferably is non-inflatable.

Preferably, the adjustment device adjusts the restriction device in a non-invasive manner. Furthermore, the adjustment device may adjust the restriction device in a non-manual manner and/or in a non-magnetic manner, i.e. magnetic forces may not be involved when adjusting the restriction device.

Furthermore, as opposed to prior art impotence treatment devices the adjustment device of the invention preferably is non-manually operated, i.e. not operated by manual forces or manipulated by touching the skin of the patient, such as by manually compressing a fluid containing balloon implanted in the scrotum. Instead the apparatus of the invention may further comprise a powered operation device for operating the adjustment device.

In the various embodiments hereinafter described the restriction device generally forms an at least substantially closed loop. However, the restriction device may take a variety of different shapes, such as the shape of a square, rectangle or ellipse. The substantially closed loop could for example be totally flat, i.e. thin as seen in the radial direction. The shape of restriction device may also be changed during use, by rotation or movements of the restriction device in any direction.

A physical lumen, such as the corpus cavernosum, crura of the penile tissue or the prolongation thereof, is often easier to restrict by contracting at least two opposite or different side walls of the lumen against each other. The expression "penile tissue and the prolongation thereof" should be understood to mean the penile tissue extended inside the human body and following the pathway of the blood flow leaving the penis i.e. one or several exit veins from the penis, corpus cavernosum, crura or the prolongation thereof. Thus, the restriction device may be designed to perform such a contracting effect of the opposite walls also of a exit vein in the penile prolongation.

Alternatively, the restriction device may comprise an adjustable cuff, a clamp or a roller for bending the vein, corpus cavernosum, crura or the prolongation thereof to restrict the blood flow therein. Such a cuff, clamp or roller may also be utilised for squeezing the vein, corpus cavernosum, crura or the prolongation thereof against human material inside the body of the patient or against implanted structures of the apparatus.

Preferably, the restriction device comprises an elongated restriction member and forming means for forming the restriction member into at least a substantially closed loop around said portion of the tissue, wherein the loop defines a restriction opening, whereby the adjustment device adjusts the restriction member in the loop to change the size of the restriction opening.

The restriction device may be implanted in the base of the patient's penis or the prolongation thereof and preferably may engage the corpus cavernosum, crura or the prolongation thereof of the penis. However, there are several alternative positions of the restriction device that give more or less satisfactory restriction of the blood flow leaving the penis. Thus, as a first alternative the restriction member may extend around both corpora cavernosa or crura of the penis as a single unit. As a second alternative the restriction device may comprise two elongated restriction members extending around respective corpora cavernosa or crura of the patient. As a third alternative the elongated restriction member may encircle one of the exit veins from the penis. As a fourth alternative the restriction device may comprise several restriction members extending around respective exit veins from the penis.

The adjustment device may be incorporated in the restriction device as well as be controlled by hydraulic means.

In accordance with a preferred first adjustment principle, the adjustment device mechanically adjusts the longitudinal extension of the elongated restriction member in a loop form.

In a preferred embodiment of the invention utilising the first adjustment principle, the restriction member comprises a main portion and two elongated end portions, and the adjustment device establishes longitudinal relative displacement between the end portions of the restriction member, so that the size of the restriction opening is adjusted. The forming means may comprise any suitable known or conventional device capable of practising the desired function, such as a spring material forming the elongated restriction member into the loop, so that the restriction opening has a predetermined size, and the adjustment device may adjust the restriction member against the spring action of the spring material. In other words, the restriction member may comprise a spring clip. The spring material may be integrated in the restriction member.

Preferably, the adjustment device comprises a movement transferring member, suitably a drive wheel, in engagement with at least one of the end portions of the restriction member and operable to displace the one end portion relative to the other end portion of the restriction member. The drive wheel may advantageously be in engagement with both of the end portions of the restriction member and be operable to displace said end portions relative to each other. An elongated flexible drive shaft may be operatively connected to the drive wheel, for transferring manual or motor generated power from a location remote from the restriction member. In its simplest embodiment, the drive wheel may comprise a pulley in frictional engagement with the restriction member. As an alternative, a gear rack may be formed on at least one of the end portions of the restriction member and the drive wheel may comprise a gear wheel in mesh with the gear rack. Other suitable known or conventional mechanisms may also or alternatively be used as the adjustment device.

The movement transferring member may alternatively comprise at least one cylinder and a piston, which is movable therein and is connected to one of the end portions of the restriction member, the piston being operable to longitudinally displace the one end portion of the restriction member relative to the other end portion of the restriction member. Alternatively, the movement transferring means may comprise two interconnected cylinders and two pistons in the respective cylinders connected to said end portions, respectively, of the restriction member, the pistons being operable to longitudinally displace the end portions of the restriction member relative to each other. Other known or conventional devices also or alternatively can be used as the movement transferring member.

A motor, which is fixed relative to the main portion of the restriction member and has a rotating drive shaft operatively connected to the movement transferring member, may be positioned relative to the elongated restriction member such that the drive shaft extends transverse thereto. Alternatively, the motor may be positioned relative to the elongated restriction member such that the drive shaft extends substantially tangentially to the loop of the restriction member.

In another embodiment of the invention utilizing the first adjustment principle, the elongated restriction member is longitudinally resilient and the adjustment device comprises a contraction device for longitudinally contracting the resilient restriction member. Preferably, the elongated restriction member comprises a substantially non-resilient main portion and an end portion forming an elongated helical spring, which is contractible by the contraction device. The contraction device may suitably comprise an elongated flexible pulling member connected to the main portion of the restriction member and extending through the helical spring to contract the helical spring against an arresting member, which is fixed relative to the main portion of the restriction member. The pulling member may extend in an elongated tube joined at one end thereof to the arresting member, so that a motor remote from the restriction member may be attached to the other end of the elongated tube and pulls the pulling member through the tube to contract the helical spring.

In yet another embodiment of the invention utilizing the first adjustment principle, the elongated restriction member comprises an elongated helical spring having a free end, and a body to which the spring is nonrotatably secured at its opposite end. The adjustment device rotates the helical spring in one direction to enlarge the coils of the helical spring to longitudinally contract the spring and to rotate the spring in the opposite direction to reduce the size of the coils of the spring to longitudinally extend the spring. As a preferred alternative, the restriction member comprises a further elongated helical spring having a free end and nonrotatably secured to the body at its opposite end, and the adjustment device comprises a drive shaft having two opposite end portions connected to the springs, respectively, at their free ends, the helical coils forming left and right hand helices, respectively. The adjustment device may alternatively comprise a gearing having an input shaft and two opposite aligned output shafts connected to the helical springs, respectively, at their free ends, the input shaft being connected to said output shafts so that the output shafts rotate in the opposite directions upon rotation of the input shaft, the helical coils forming the same helices.

In accordance with a second adjustment principle, the adjustment device mechanically adjusts the restriction member so that at least a portion of a radially innermost circumferential confinement surface formed by the restriction member is substantially radially displaced.

In one embodiment of the invention utilizing the second adjustment principle, the restriction member comprises an elongated voltage responsive element forming part of the confinement surface and capable of bending into a bow in response to a voltage applied across the element, the radius of curvature of the bow being adjustable by changing the level of the voltage.

In another embodiment of the invention utilizing the second adjustment principle, the adjustment device changes the diameter of an elastic annular element of the restriction member, which forms the confinement surface. Preferably, the forming means comprises a substantially rigid outer annular element coaxially surrounding the elastic annular element, and the adjustment device comprises means for pulling the elastic annular element radially outwardly towards the outer annular element to expand the elastic annular element. For example, the pulling means may comprise a plurality of threads secured to the elastic annular element along the circumference thereof and running from the elastic annular element via guide members attached to the outer annular element.

In yet another embodiment of the invention utilizing the second adjustment principle, the forming means comprises a substantially rigid outer annular element, and the restriction member comprises an elongated helical spring extending internally along the outer annular element and contacting the latter. The helical spring forms part of the circumferential confinement surface and has a free end. The restriction member further comprises a body to which the spring is nonrotatably secured at its opposite end. The adjustment device rotates the helical spring in one direction to enlarge the coils of the spring to contract the circumferential confinement surface and rotates the spring in the opposite direction to reduce the size of the coils of the spring to expand the circumferential confinement surface. As an alternative, which is preferred, the restriction member comprises two elongated helical springs forming part of the circumferential confinement surface and connected to the body of the restriction member. The adjustment device rotates each spring in one direction to enlarge the coils of the spring to contract the circumferential confinement surface and rotates the spring in the opposite direction to reduce the size of the coils of the spring to expand the circumferential confinement surface.

In accordance with a third adjustment principle, the restriction member comprises at least two separate elements, at least one of which is pivoted so that it may turn in a plane in which the restriction member extends, and the adjustment device turns the pivoted element to change the size of the restriction opening. Preferably, the restriction member comprises a plurality of separate pivoted elements disposed in series, each pivoted element being turnable in the plane, and the adjustment device turns all of the pivoted elements to change the size of the restriction opening. For example, the pivoted elements may comprise lamellae arranged like the conventional adjustable aperture mechanism of a camera.

In accordance with a fourth adjustment principle, the adjustment device folds at least two foldable frame elements of the restriction member towards each other. Preferably, the foldable frame elements comprise two substantially or partly semi-circular frame elements which are hinged together so that the semi-circular elements are swingable relative to each other from a fully open state in which they form part of a circle to a fully folded state in which they form part of a semi-circle. The same principal may be used with the swingable parts mounted together in one end and not in the other end. Alternatively, the restriction device may comprises two preferable rigid articulated clamping elements positioned on opposite sides of a vein like the blades of a scissor, and the adjustment device turns the clamping elements toward each other to clamp the vein, corpus cavernosum, crura or the prolongation thereof between the clamping elements, thereby restricting the blood flow in the vein, corpus cavernosum, crura or the prolongation thereof.

In accordance with a fifth adjustment principle, the adjustment device turns the restriction member around a longitudinal extension thereof, the elongated restriction member being elastic and varying in thickness as seen in a cross-section therethrough. Suitably, the elongated restriction member comprises an elastic belt.

In accordance with a sixth adjustment principle, the adjustment device changes the size of the restriction opening such that the outer circumferential confinement surface of the restriction member is changed.

In accordance with a seventh adjustment principle, the adjustment device changes the size of the restriction opening such that the outer circumferential confinement surface of the restriction member is unchanged.

In accordance with an eighth adjustment principle, the elongated restriction member may be flexible, and the adjustment device pulls a first portion of the flexible restriction member from a second portion of the flexible restriction member opposite the first portion in the loop to squeeze a vein, the corpus cavernosum, the crura or the prolongation thereof between two opposite lengths of the elongated flexible restriction member to restrict the blood flow in the vein, corpus cavernosum, crura or the prolongation thereof.

In accordance with a ninth adjustment principle, the restriction device comprises two rigid elements on opposite or different sides of a vein, the corpus cavernosum, the crura or the prolongation thereof, and the adjustment device decreases the distance between the rigid elements to squeeze the vein, corpus cavernosum, crura or the prolongation thereof between the rigid elements, thereby restricting the blood flow in the vein, corpus cavernosum, crura or the prolongation thereof.

In accordance with a tenth adjustment principle, the restriction device bends or rotates a portion of a vein, the corpus cavernosum, the crura or the prolongation thereof to restrict the blood flow in the same. For example, the restriction device may comprise at least two bending members, such as cylindrical or hour-glass shaped rollers, positioned on opposite or different sides of the vein and displaced relative to each other along the vein, corpus cavernosum, crura or the prolongation thereof, and the adjustment device may move the bending members against the vein, corpus cavernosum, crura or the prolongation thereof to bend the latter to restrict the blood flow in the vein, corpus cavernosum, crura or the prolongation thereof. Suitably, the displacement members may comprise rollers. The restriction device may also rotate a portion of the esophagus or stomach. The bending or rotating members may take any shape. With the prolongation of the corpus cavernosum or crura should be understood the penile tissue extended inside the human body and following the pathway of the blood flow leaving the penis.

Alternatively, the two bending members one placed more distal than the other may be rotated in opposite direction relative to each other. With interconnecting material for example flexible bands between the holding members a restriction will occur between the bending members when they are rotated.

The restriction device may in all applicable embodiments take any shape and be either hydraulic or non-inflatable.

In all of the above-described embodiments of the invention the adjustment device is conveniently operated by any suitable motor, preferably an electric motor, which may be fixed directly to or be placed in association with the restriction device, or alternatively be located remote from the restriction device, advantageously in the abdomen or subcutaneously. In the latter alternative the motor is advantageously connected to the adjustment device by a flexible power transmission conduit to permit a suitable positioning of the motor in the abdomen of the patient. The motor may be manually activatable, for example by an implanted switch.

In some of the above described embodiments of the invention, however, the adjustment device may conveniently be operable by a hydraulic operation device, which preferably is manually activatable. The hydraulic operation device may advantageously include hydraulic servo means to facilitate manual activation. As an alternative, the hydraulic device may be powered by an electric motor, which may be manually activatable or controlled by remote control means. The components of such a hydraulic operation device may be placed in association with the restriction device and/or be located at a suitable place in the abdomen or subcutaneously.

More specifically, a reservoir may be provided containing a predetermined amount of fluid for supplying the hydraulic operation device with fluid. The reservoir defines a chamber for the predetermined amount of fluid and the hydraulic operation device changes the size of the chamber. The hydraulic operation device may comprise first and second wall portions of the reservoir, which are displaceable relative to each other to change the size of the chamber of the reservoir. The first and second wall portions of the reservoir may be designed to be displaceable relative to each other by manual manipulation thereof, preferably to permit manual pushing, pulling or rotation of any of the wall portions in one direction. Alternatively, the wall portions may be displaceable relative to each other by magnetic means (such as a permanent magnet and magnetic material reed switch, or other known or conventional magnetic devices), hydraulic means or electrical control means such as an electric motor. The magnetic means, hydraulic means, or electrical control means may all be activated by manual manipulation, preferably using a subcutaneously located manually manipulatable device. This control may be indirect, for example via a switch.

The hydraulic operation device may operate the adjustment device with fluid from the reservoir in response to a predetermined first displacement of the first wall portion of the reservoir relative to the second wall portion of the reservoir, to adjust the restriction device to release the tissue, and to operate the adjustment device with fluid from the reservoir in response to a predetermined second displacement of the first wall portion of the reservoir relative to the second wall portion of the reservoir, to adjust the restriction device to restrict the blood flow leaving the penis. In this embodiment, no pump is used, only the volume of the reservoir is varied. This is of great advantage compared to the solution described below when a pump is used to pump fluid between the reservoir and the adjustment device because there is no need for a non-return valve and it is still possible to have fluid going both to and from the reservoir.

As an alternative, the hydraulic operation device may comprise a pump for pumping fluid between the reservoir and the adjustment device. The pump may pump fluid both to and away from the adjustment device, or hydraulic means controlling the adjustment device. A mechanical manual solution is proposed in which it is possible to pump in both directions just by pushing an activating member in one direction. Another alternative is a pump pumping in only one direction and an adjustable valve to change the direction of fluid to either increase or decrease the amount of fluid in the reservoir. This valve may be manipulated manually, mechanically, electrically, magnetically, or hydraulically. Any kind of motor could of course be used for all the different operations as well as wireless remote solutions. The pump may comprise a first activation member for activating the pump to pump fluid from the reservoir to the adjustment device and a second activation member for activating the pump to pump fluid from the adjustment device to the reservoir. The activation members may be operable by manual manipulation, preferably to permit manual pushing, pulling or rotating thereof in one direction. Suitably, at least one of the activation members is adapted to operate when subjected to an external pressure exceeding a predetermined magnitude.

Alternatively, at least one of the first and second activating members may be operable by magnetic means, hydraulic means or electrical control means such as an electric motor. The magnetic means, hydraulic means, or electrical control means may all be activated by manual manipulating means preferably located subcutaneously. This activation may be indirect, for example via a switch.

Advantageously, especially when manual manipulation means are used, a servo means could be used. With servo means less force is needed for operating the adjustment device. The term "servo means" encompasses the normal definition of a servo mechanism, i.e. an automatic device that controls large amounts of power by means of very small amounts of power, but may alternatively or additionally encompass the definition of a mechanism that transfers a weak force acting on a moving element having a long stroke into a strong force acting on another moving element having a short stroke. The servo means may comprise a motor, preferably an electric motor, which may be reversible.

Alternatively, a reverse servo may be employed. The term "reverse servo" is to be understood as a mechanism that transfers a strong force acting on a moving element having a short stroke into a weak force acting on another moving element having a long stroke; i.e. the opposite function of the above-defined alternative mechanism of a normal servo mechanism. A first closed hydraulic system that controls another closed hydraulic system in which hydraulic means of the adjustment device is incorporated may be used. Minor changes in the amount of fluid in a smaller reservoir of the first system could then be transferred by the reverse servo into major changes in the amount of fluid in a larger reservoir in the second system. In consequence, the change of volume in the larger reservoir of the second system will affect the hydraulic means of the adjustment device. For example, a short stroke that decreases the volume of the smaller reservoir will cause the larger reservoir to supply the adjustment device with a large amount of hydraulic fluid, which in turn results in a long mechanical adjustment stroke on the restriction device. The great advantage of using such a reverse servo is that the larger volume system could be placed inside the abdomen or retroperitoneum where there is more space and still it would be possible to use manual manipulation means of the smaller system subcutaneously. The smaller reservoir could be controlled directly or indirectly by a fluid supply means. The fluid supply means may include another small reservoir, which may be placed subcutaneously and may be activated by manual manipulation means. Both the servo and reverse servo may be used in connection with all of the various components and solutions described in the present specification.

Preferably, the reverse servo comprises hydraulic means and a main fluid supply reservoir and eventually an additional fluid supply reservoir. Both reservoirs define a chamber containing hydraulic fluid, and the hydraulic means comprises first and second wall portions of the main fluid supply reservoir, which are displaceable relative to each other to change the volume of the chamber of the main fluid supply reservoir. The hydraulic means may control the adjustment device indirectly, e.g. via an increased amount of fluid in the main fluid supply reservoir, in response to a predetermined first displacement of the first wall portion of any of the reservoirs relative to the second wall portion of the reservoir to restrict the blood flow leaving the penis, and to control the adjustment device in response to a second displacement of the first wall portion of any reservoir relative to the second wall portion, to indirectly adjust the restriction device to release the penile tissue. The wall portions of the reservoirs may be designed to be displaceable relative to each other by manual manipulation thereof or be displaceable relative to each other by manually pushing, pulling or rotating any of the wall portions of the reservoir in one direction. Alternatively, the wall portions of the main fluid supply reservoir may be displaceable relative to each other by magnetic means, hydraulic means or electric control means including an electric motor.

The magnetic means, hydraulic means, or electrical control means may all be activated by manually manipulated means preferably located subcutaneously. This control may be indirect for example via a switch.

Even in the broadest embodiment of the invention the adjustment device may comprise a servo means. The servo means may comprise a hydraulic operation means, an electrical control means, a magnetic means, mechanical means or a manual manipulation means. The hydraulic operation means, electrical control means, mechanical means or magnetic means may be activated by manual manipulating means. Using a servo system will save the use of force when adjusting the adjustment device which may be of importance in many applications, for example when a battery cannot put out enough current although the total energy in the battery is more than enough to power the system.

In accordance with a preferred embodiment of the invention, the apparatus comprises implantable electrical components including at least one, or only one single voltage level guard and a capacitor or accumulator, wherein the charge and discharge of the capacitor or accumulator is controlled by use of the voltage level guard. As a result, there is no need for any implanted current detector and/or charge level detector for the control of the capacitor, which makes the apparatus simple and reliable.

All solutions may be controlled by a wireless remote control for controlling the adjustment device. The remote control may advantageously be capable of obtaining information related to the blood flow leaving the penis or the blood pressure or other important physical parameters and of commanding the adjustment device to adjust the restriction device in response to obtained information. With the wireless remote control the apparatus of the invention is conveniently controlled by the patient when he so desires, which is of great advantage compared to the prior art procedures. With the remote control the apparatus of the invention is conveniently controlled to adjust the implanted restriction device, which controls the blood flow leaving the penis. The restriction device may be operable to open and close the blood flow passageway formed by the penile exit veins. The restriction device may steplessly control the cross-sectional area of the passageway.

The apparatus may further comprise a pressure sensor for directly or indirectly sensing the pressure against the restriction device and the restriction device may control the blood flow in response to signals from the pressure sensor. The pressure sensor may be any suitable known or conventional pressure sensor such as shown in U.S. Pat. No. 5,540,731, 4,846,181, 4,738,267, 4,571,749, 4,407,296 or 3,939,823; or an NPC-102 Medical Angioplasty Sensor. The adjustment device preferably non-invasively adjusts the restriction device to change the size of the cross-sectional area.

The adjustment device and/or other energy consuming components of the apparatus may be energised with wirelessly transmitted energy from outside the patient's body or be powered by an implanted battery or accumulator.

The apparatus may further comprise an implanted energy transforming device for transforming wireless energy directly or indirectly into kinetic energy for operation of the restriction device. The energy transforming device may, preferably directly, transform the wireless energy in the form of sound waves into electric energy for operation of the restriction device. Suitably the energy transforming device comprises a capacitor adapted to produce electric pulses from the transformed electric energy.

The apparatus of the invention may further comprise an energy transfer means for wireless transfer of energy from outside the patient's body to the adjustment device and/or other energy consuming implantable components of the apparatus. The energy transfer means may be adapted to intermittently transfer the energy, preferably electric energy, in the form of a train of energy pulses for direct use in connection with the energising of the energy consuming components of the apparatus. An implanted capacitor having a capacity less than 0.1 µF may be used for producing the train of energy pulses.

A motor may be implanted for operating the adjustment device, wherein the energy transfer means is adapted to directly power the motor with transferred energy. Alternatively, or in combination with the motor, a pump may be implanted for operating the adjustment device, wherein the energy transfer means is adapted to transfer wireless energy in the form of electromagnetic waves for direct power of the pump. Preferably, the pump is not a plunger type of pump, but may comprise a peristaltic or membrane pump.

The energy transfer means preferably transfers wireless energy in the form of electromagnetic waves. However, for safety radio waves may be excluded.

Alternatively, the energy transferred by the energy transfer means may comprise an electric field or a magnetic field.

Most preferred, the energy transferred by the energy transfer means comprises a signal.

Preferably, the wireless remote control comprises a separate signal transmitter or receiver and a signal receiver or transmitter implanted in the patient. For example, the signal transmitter and signal receiver may transmit and receive a signal in the form of digital pulses, which may comprise a magnetic or electric field. Alternatively, which is preferred, the signal transmitter and signal receiver may transmit and receive an electromagnetic wave signal, a sound wave signal or a carrier wave signal for a remote control signal. The receiver may comprise an implanted control unit for controlling the adjustment device in response to a control signal from the signal transmitter.

The apparatus of the invention may further comprise an implanted energiser unit for providing energy to energy consuming implanted components of the apparatus, such as electronic circuits and/or a motor for operating the adjustment device. The apparatus may comprise an external energy transmitter for transmitting wireless energy, wherein the energiser unit is adapted to transform the wireless energy into electric energy. An implanted electric motor may operate the adjustment device and the energiser unit may be adapted to power the electric motor with the electric energy transformed from the wireless energy.

The energiser unit may comprise a battery and a switch operable by the wireless energy transmitted by the external transmitter, for connecting the battery to the implanted energy consuming components of the apparatus in an "on" mode when the switch is powered by the wireless energy and to keep the battery disconnected from the energy consuming components in a "standby" mode when the switch is not powered.

The control unit may power such an implanted motor with energy provided by the energiser unit in response to a control signal received from the signal transmitter. Any known or conventional signal transmitter or signal receiver that is suitable for use with a human or mammal patient may be provided as the signal transmitter or signal receiver of the invention.

Generally, all the signals mentioned above may comprise electromagnetic waves, such as infrared light, visible light, laser light, micro waves, or sound waves, such as ultrasonic waves or infrasonic waves, or any other type of wave signals. The signals may also comprise electric or magnetic fields, or pulses. All of the above-mentioned signals may comprise digital signals. The control signals may be carried by a carrier wave signal, which in an alternative embodiment may be the same signal as the wireless energy signal. Preferably a digital control signal may be carried by an electromagnetic wave signal. The carrier wave or control signal may be amplitude or frequency modulated.

The motor may be any type of motor, such as a pneumatic, hydraulic or electric motor and the energiser unit may power the motor with pressurized gas or liquid, or electric energy, depending on the type of motor. Where the motor is an electric motor, it may power pneumatic or hydraulic equipment.

The energiser unit may comprise a power supply and the control unit may power the motor with energy from the power supply. Preferably, the power supply is an electric power supply, such as a battery, and the motor is an electric motor. In this case, the battery also continuously powers at least part of the circuitry of the signal receiver in a standby mode between the adjustments, in order to keep the signal receiver prepared for receiving signals transmitted from the signal transmitter.

The energiser unit may transfer energy from the control signal, as the control signal is transmitted to the signal receiver, into electric energy for powering the implanted electronic components. For example, the energiser unit may transfer the energy from the control signal into a direct or alternating current.

In case there is an implanted electric motor for operating the adjustment device the energiser unit may also power the motor with the transferred energy. Advantageously, the control unit directly powers the electric motor with electric energy, as the energiser unit transfers the signal energy into the electric energy. This embodiment is particularly simple and does not require any recurrent invasive measures for exchanging empty power supplies, such as batteries, that is required in the first embodiment described above. The motor may also be directly powered with wirelessly transmitted electromagnetic or magnetic energy in the form of signals, as the energy is transmitted. All the various functions of the motor and associated components described in the present specification may be used where applicable.

For adjustment devices of the type that requires more, but still relatively low, power for its operation, the energiser unit may comprise a rechargeable electric power supply for storing the electric energy obtained and the control unit may power the electric motor with energy from the rechargeable electric power supply in response to a control signal received from the signal transmitter. In this case, the rechargeable power supply can be charged over a relatively long time (e.g. a few seconds up to a half hour) without powering the electric motor.

The electric power supply suitably comprises an inexpensive simple capacitor. In this case, the electric motor may be a stepping motor. In all embodiments the motor may, preferable be able to perform a reversing function.

The signal transmitter may transmit an electromagnetic signal and the energiser unit may draw radiant energy from the electromagnetic wave signal, as the latter is transmitted to the signal receiver, and transfer the radiant energy into electric energy.

Alternatively, the energiser unit may comprise a battery or accumulator, an electrically operable switch adapted to connect the battery to the signal receiver in an on mode when the switch is powered and to keep the battery disconnected from the signal receiver in a standby mode when the switch is not powered, and a rechargeable electric power supply for powering the switch. The control unit may power the electric motor with energy from the battery in response to a control signal received from the signal transmitter, when the switch is in its on mode. Advantageously, the energiser unit may transform wave energy from the control signal, as the latter is transmitted to the signal receiver, into a current for charging the rechargeable electric power supply, which suitably is a capacitor. Energy from the power supply is then used to change the switch from off (standby mode) to on. This embodiment is suited for adjustment devices of the type that require relatively high power for their operation and has the advantage that the electronic circuitry of the signal receiver does not have to be powered by the battery between adjustments. As a result, the lifetime of the battery can be significantly prolonged. The switch may be switched manually or by the use of magnetic or electric energy.

As an example, the signal transmitter may transmit an electromagnetic wave signal and the energiser unit may draw radiant energy from the electromagnetic wave signal, as the latter is transmitted to the signal receiver, and may transfer the radiant energy into said current. The energiser unit suitably comprises a coil of the signal receiver for inducing an alternating current as the electromagnetic wave signal is transmitted through the coil and a rectifier for rectifying the alternating current. The rectified current is used for charging the rechargeable power source.

Alternatively, the signal transmitter and receiver may solely be used for a control signal and a further pair of signal transmitter and receiver may be provided for transferring signal energy to implanted components. By such a double system of signal transmitters and receivers) the advantage is obtained that the two systems can be designed optimally for their respective purposes, namely to transmit a control signal and to transfer energy from an energy signal. Accordingly, the apparatus may further comprise an external energy transmitter for transmitting wireless energy, wherein the energiser unit comprises a battery and an operable switch for connecting the battery to the signal receiver in an "on" mode when the switch is powered and for keeping the battery disconnected from the signal receiver in a "standby" mode when the switch is not powered, and the external energy transmitter powers the switch. Suitably, the energy transmitter may directly power the switch with the wireless energy to switch into the "on" mode. As should be realized by a skilled person, in many of the above-described embodiments of the invention the adjustment device may be operated by control means or manual manipulation means implanted under the skin of the patient, such as a pump, an electrical switch or a mechanical movement transferring means. In the manual embodiment it is not necessary to use a motor for operating the adjustment device.

In embodiments including hydraulic transmission means, an injection port connected to the hydraulic means may be provided for enabling, normally single, once-and-for-all, calibration of the amount of fluid in the hydraulic system.

In all embodiments a motor may be operatively connected to the adjustment device. A reversing device may be implanted in the patient for reversing the motor. The adjustment device preferably adjusts the restriction device in a non-manual manner without the patient touching his skin.

The adjustment device may be adapted to hydraulically adjust the restriction device by using hydraulic means which is devoid of hydraulic fluid of the kind having a viscosity that substantially increases when exposed to heat or a magnetic field, i.e. the hydraulic fluid would not become more viscous when exposed to heat or influenced by magnetic forces.

All the above-described various components, such as the motor, pump and capacitor, may be combined in the different embodiments where applicable. Also the various functions described in connection with the above embodiments of the invention may be used in different applications, where applicable.

All the various ways of transferring energy and controlling the energy presented in the present specification may be practised by using all of the various components and solutions described.

The invention also provides a method for treating male sexual impotence, comprising surgically implanting in the body of a male patient suffering from sexual impotence an adjustable restriction device which directly engages a portion of the normal penile tissue of the patient to affect the blood flow leaving the penis and the prolongation thereof, and when desired to achieve erection, mechanically adjusting the restriction device to temporarily restrict the blood flow leaving the penis.

The method may further comprise implanting the male sexual impotence treatment apparatus in the base of the patient's penis or its prolongation, preferably implanting an restriction device engaging the corpora cavernosa, crura or the prolongation thereof as a single unit or engaging the two corpora cavernosa or crura or the prolongations thereof separately. The method may comprise implanting the restriction device engaging one or both of the crura of the penis.

As a modification, the method may further comprise implanting the restriction device engaging at least one of the exit veins from the penis.

The invention provides another method for treating male sexual impotence, comprising the steps of: placing at least two laparascopical trocars in the body of a male patient suffering from sexual impotency, inserting a dissecting tool through the trocars and dissecting an area of the penis and abdominal or peritoneal surroundings, placing at least one adjustable restriction device in the dissected area engaging the penile tissue or the prolongation thereof, and adjusting the restriction device to restrict the blood flow leaving the penis when the patient wishes to achieve erection.

The method may further comprise mechanically adjusting said restriction device in a non-manual manner. The restriction device may engage (a) both of the corpora cavernosa, the crura of the penis or the prolongation thereof as a single unit; or (b) one of the exit veins from the penis.

Alternatively, the method may further comprise implanting (a) a further adjustable restriction device, wherein the two restriction devices engage the two corpora cavernosa, the crura of the penis or their prolongations, respectively, as separate units; or (b) several restriction devices engaging respective exit veins from the penis.

The method may further comprise implanting a source of energy in the patient and providing a control device for controlling the source of energy from outside the patient's body to supply energy to the restriction device.

The invention is described in more detail in the following with reference to the accompanying drawings, in which FIG. 1 is a schematic sectional view of a preferred first embodiment of the male sexual impotence treatment apparatus in accordance with the invention;

FIGS. 2 and 3 are cross-sectional views taken along the lines II-II and III-III, respectively, of FIG. 1;

FIGS. 4 and 5 schematically show two alternative designs of the embodiment of FIG. 1;

FIG. 6 schematically illustrates a motor arrangement for the design according to FIG. 5;

FIG. 7 is a schematic sectional view of a second embodiment of the apparatus in accordance with the invention;

FIG. 8 schematically illustrates a hydraulic transmission conduit for the embodiment of FIG. 7;

FIG. 9 is a schematic sectional view of a third embodiment of the apparatus in accordance with the invention;

FIG. 10 is a modification of the embodiment of FIG. 9;

FIG. 11 is a schematic view of a fourth embodiment of the apparatus in accordance with the invention;

FIGS. 12 and 13 are enlarged details of the embodiment of FIG. 11;

FIG. 14 is a cross-section along the line XIV-XIV of FIG. 11;

FIG. 15 is a schematic view of a fifth embodiment of the apparatus in accordance with the invention;

FIG. 16 is an enlarged detail of FIG. 15;

FIG. 17 is a cross-section along the line XVII-XVII of FIG. 15;

FIGS. 18 to 21 are schematic sectional views of a sixth, seventh, eighth and ninth embodiments, respectively, of the apparatus in accordance with the invention;

FIGS. 22 and 23 illustrate a fully open and a reduced restriction opening, respectively, of the embodiment of FIG. 21;

FIG. 24 is a schematic view of a tenth embodiment of the apparatus in accordance with the invention;

FIG. 25 is an enlarged detail of the embodiment of FIG. 24;

FIGS. 26 and 27 illustrate a fully open and a reduced restriction opening, respectively, of the embodiment of FIG. 24;

Figure 28:
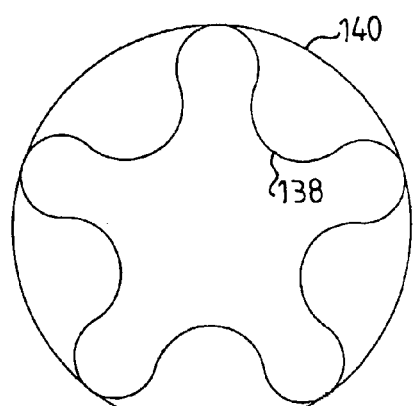
Figure 29A:
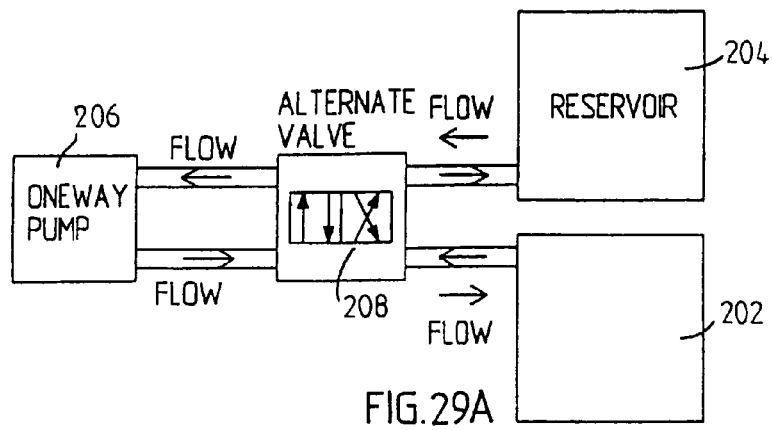
Figure 29B:
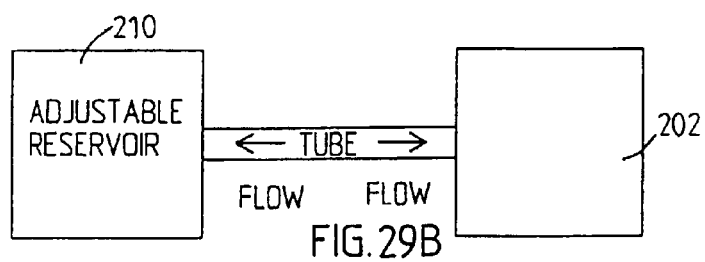
Figure 29C:
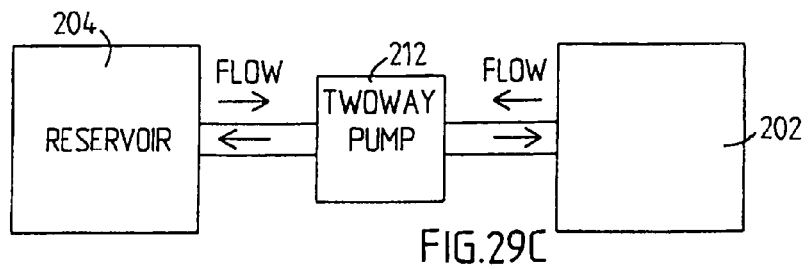
Figure 29D:
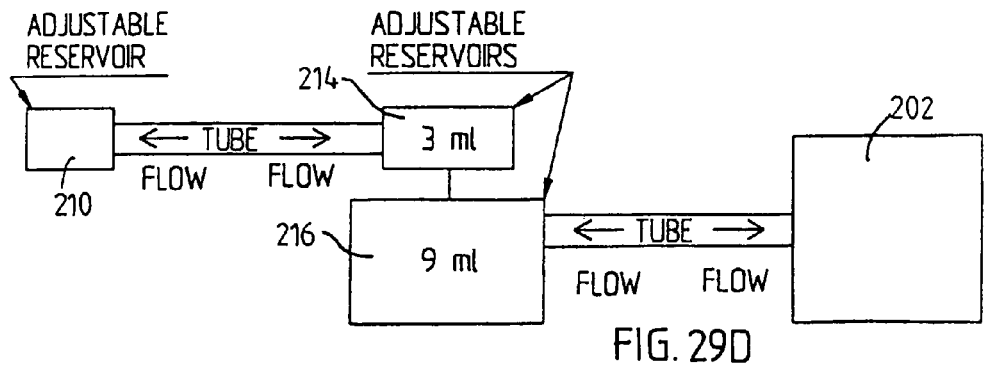
Figure 30A:
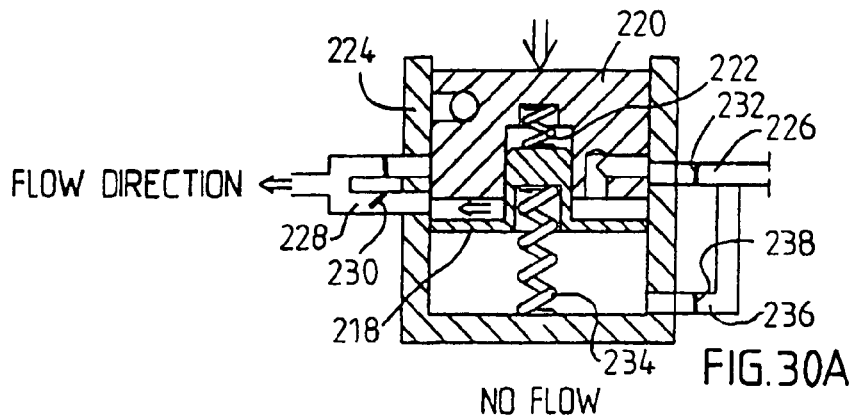
Figure 30B:
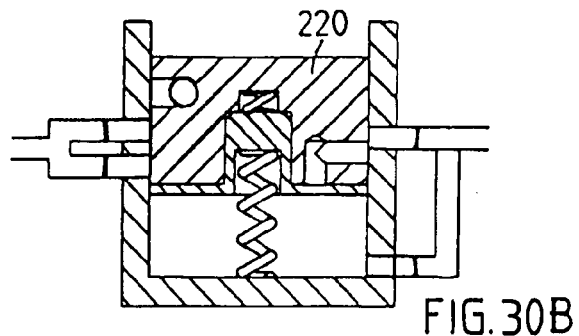
Figure 34:
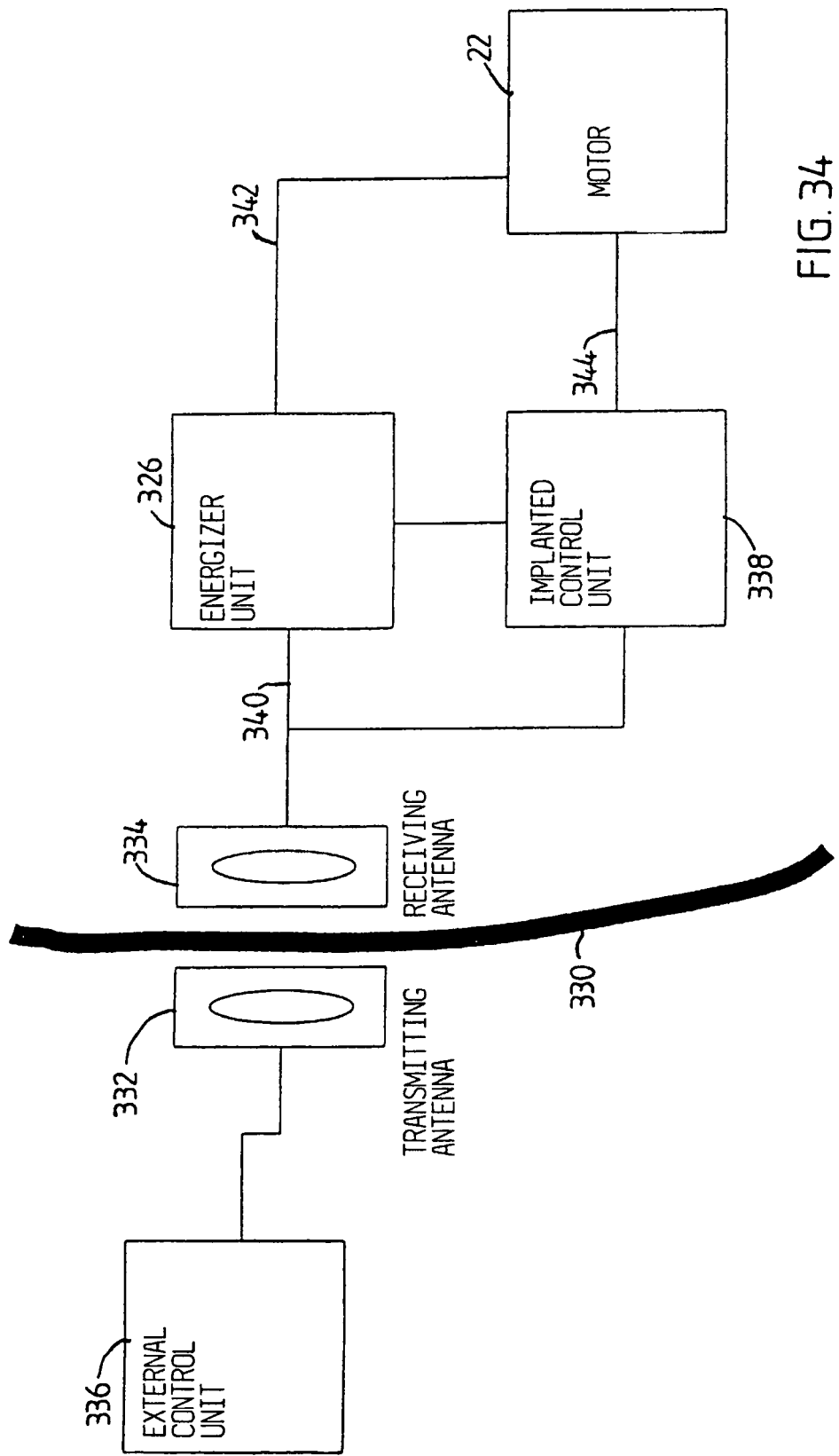
Figure 35:
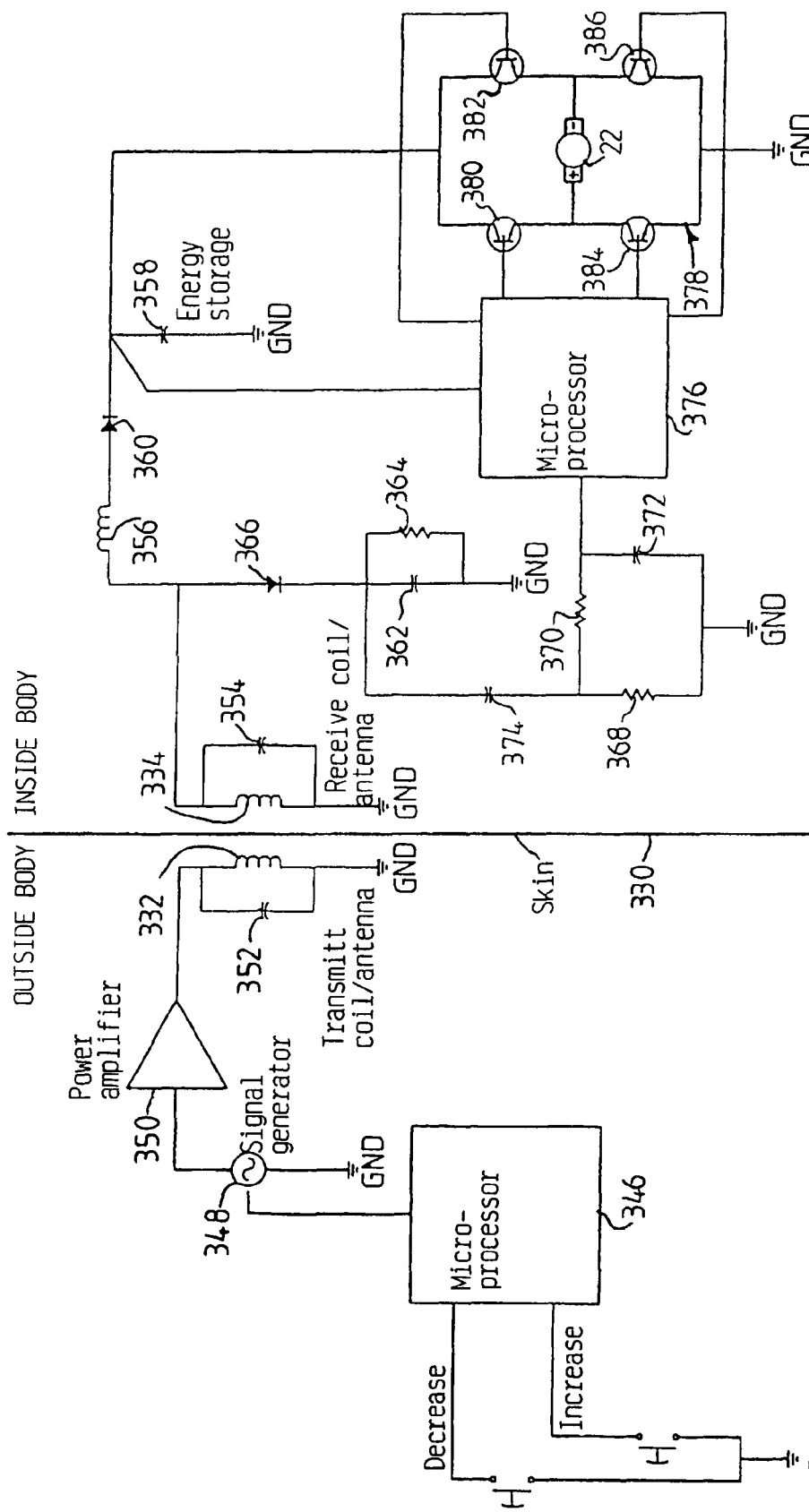
Figure 36A:
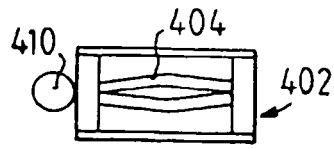
Figure 37A:
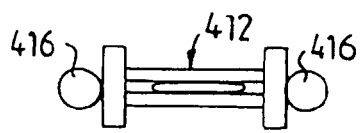
Figure 36B:
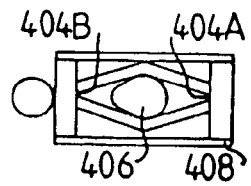
Figure 37B:
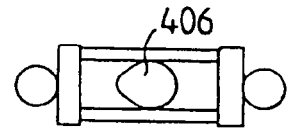
Figure 38:
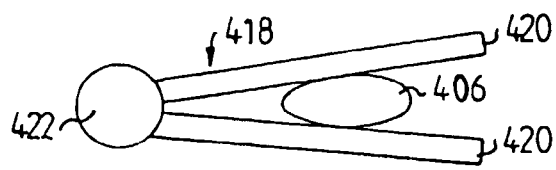
Figure 39A:
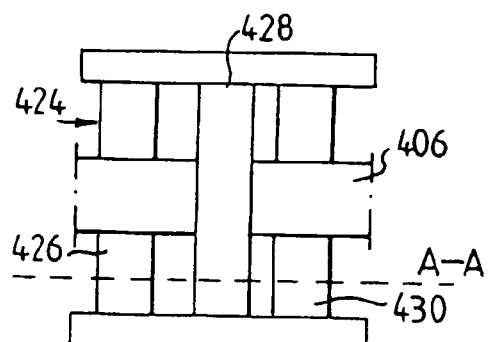
Figure 39B:
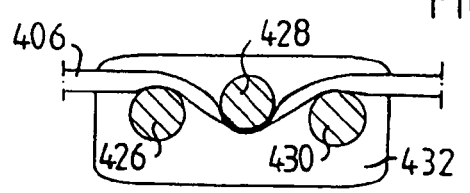
Figure 39C:
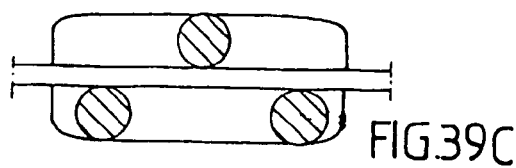
Figure 45:
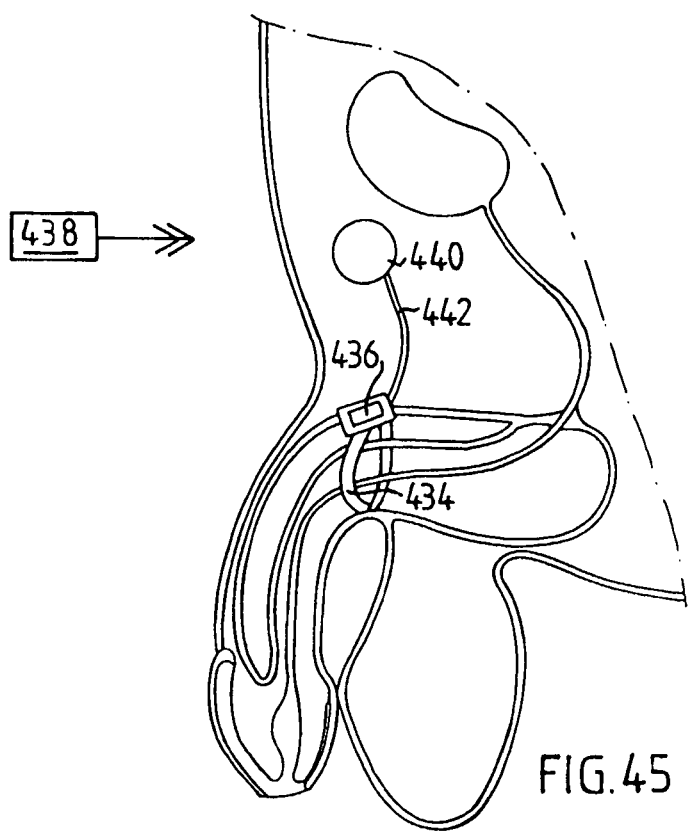
Figure 46:
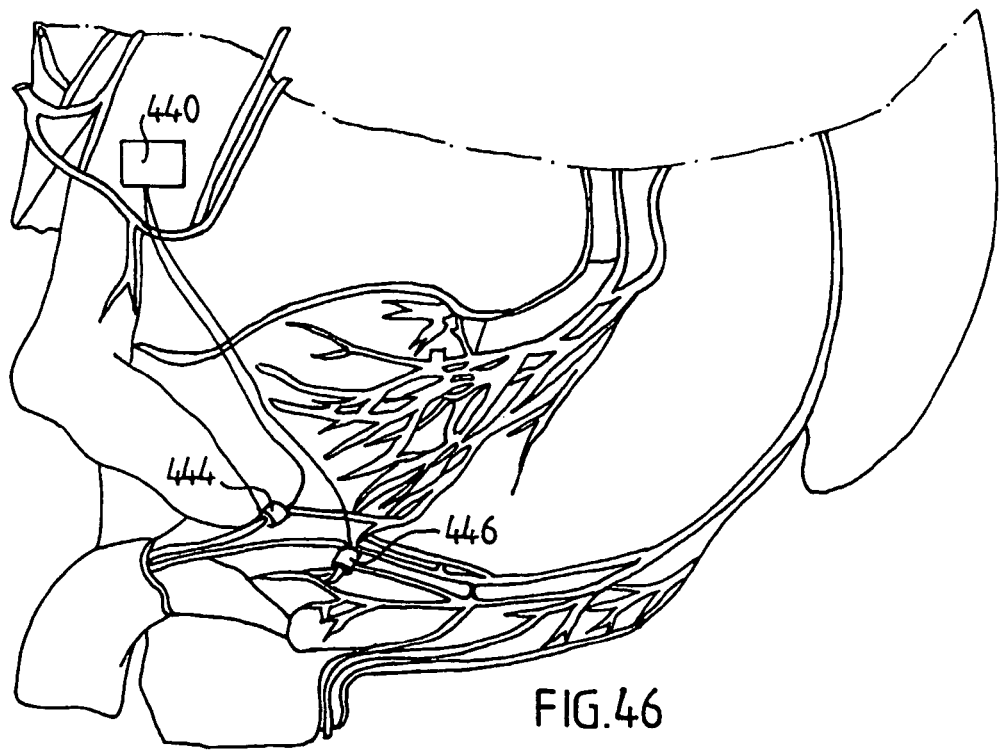

FIG. 28 schematically illustrates a cushion arrangement for protecting the tissue of the patient;

FIG. 29A-D is a block diagram of four different principal embodiments of the invention;

FIG. 30A-D are cross-sectional views of a pump mechanism according to FIG. 29C, which pumps fluid in opposite directions by mechanically pushing a wall portion in only one direction;

FIG. 31 is a cross-sectional view of a reservoir having a variable volume controlled by a remote control motor, in accordance with a particular embodiment of the principal embodiment shown in FIG. 29B or 30B;

FIG. 32 is a cross-sectional view of a reservoir having a variable volume adjustable by manual manipulation, in accordance with a particular embodiment of the principal embodiment shown in FIG. 29B or 29D;

FIG. 33A is a front view of a hydraulic, pneumatic or mechanical reverse servo system in accordance with a particular embodiment of the principal embodiment shown in FIG. 29D;

FIG. 33B is a cross-sectional view taken along line VB-VB of FIG. 33A;

FIG. 34 is a block diagram illustrating remote control components of the apparatus of the invention;

FIG. 35 is a schematic view of a circuitry used for the system of the block diagram of FIG. 34;

FIGS. 36A and 36B are schematic views of an eleventh embodiment of the apparatus in accordance with the invention;

FIGS. 37A and 37B are schematic views of a twelfth embodiment of the apparatus in accordance with the invention;

FIG. 38 is a schematic view of a thirteenth embodiment of the apparatus in accordance with the invention;

FIGS. 39A, 39B and 39C are a schematic front view and schematic sectional views, respectively, of a fourteenth embodiment of the apparatus in accordance with the invention;

FIGS. 40A through 44B are five modifications of the embodiment of FIGS. 39A-39C;

FIG. 45 illustrates the apparatus of the invention with a restriction device implanted around the corpus cavernosum of a patient; and FIG. 46 illustrates the apparatus of the invention with two restriction members implanted around respective exit veins from the penis of a patient.

Referring to the drawing figures, like reference numerals designate identical or corresponding elements throughout the several figures.

FIGS. 1-3 show a preferred embodiment of the male sexual impotence treatment apparatus of the invention comprising a restriction device having an elongated restriction member in the form of a circular resilient core 2 with two overlapping end portions 4,6. The core 2 defines a substantially circular restriction opening and is enclosed in an elastic soft hose 8 except at a releasable and lockable joint 10 of the core 2, which when released enables application of the core 2 with its hose 8 around a tissue of a patient, such as the corpus cavernosum or one or more exit veins from the patient's penis. The materials of all of these elements are bio-compatible so that the patient's body will not reject them. A mechanical adjustment device 12 for mechanically adjusting the longitudinal extension of the core 2 to change the size of the restriction opening comprises a drive wheel 14 in frictional engagement with the overlapping end portions 4,6 of the core 2. The drive wheel 14 is journalled on a holder 16 placed in the hose 8 and provided with two counter pressure rollers 18,20 pressing the respective end portions 4, 6 of the core 2 against the drive wheel 14 to increase the frictional engagement therebetween. An electric motor 22 is connected to the drive wheel 14 via a long flexible drive shaft 24 and is moulded together with a remote controlled power supply unit 26 in a body 28 of silicone rubber. The length of the flexible drive shaft 34 is selected so that the body 28 can be placed in a desired position in the patient's body, suitably in the abdomen.

When the patient wishes to achieve erection, he controls the power supply unit 26 to power the electric motor 22 to turn the drive wheel 14 in one direction to reduce the diameter of the core 2, so that the penile tissue is squeezed and the blood flow leaving the penis is restricted. When the patient wishes to regain flaccid condition of his penis, he controls the power supply unit 26 to power the electric motor 22 to turn the drive wheel 14 in the opposite direction to increase the diameter of the core 2, so that the tissue is released.

Alternatively, a rack gear may be formed on one of the end portions 4,6 of the core 2 and the drive wheel 14 may be replaced by a drive gear wheel connected to the other end portion of the core 2 and in mesh with the rack gear.

FIG. 4 shows an embodiment of the invention which is identical to the embodiment of FIGS. 1-3, except that the motor 22 is encapsulated in a lateral protrusion 30 of the hose 8 so that it is fixed to the core 2 and has a short drive shaft 32 onto which the drive wheel 14 is mounted, and that the motor 22 is positioned relative to the circular core 2 such that the drive shaft 32 extends radially thereto.

FIG. 5 shows an embodiment of the invention which likewise is identical to the embodiment of FIGS. 1-3, except that the motor 22 is encapsulated in the hose 8 so that it is fixed to the core 2 and has a short drive shaft 32, and that the motor 22 is positioned relative to the core 2 such that the drive shaft 32 extends substantially tangentially to the circular core 2. There is an angular gearing 34 connecting the drive shaft 32 to the drive wheel 14.

FIG. 6 shows a suitable arrangement for the motor 22 in the embodiment of FIG. 5, comprising a first clamping member 36 secured to one end portion of the core 2 and a second clamping member 38 secured to the other end portion 6 of the core 2. The motor 22 is secured to the first clamping member 36 and is operatively connected to a worm 40 via a gear transmission 42. The worm 40 is journalled at its opposite ends on holders 44 and 46, which are rigidly secured to the clamping member 36 and the motor 22, respectively. The second clamping member 38 has a pinion in mesh with the worm 40. When the motor 22 is powered the worm 40 rotates and will thereby pull the end portion 6 of the core 2 in one or the opposite longitudinal direction, so that the diameter of the substantially circular core 2 is either increased or decreased.

FIG. 7 shows an embodiment of the invention in which the elongated restriction member comprises a core 48 and a helical spring 50. A spring contracting means in the form of a flexible pulling member 52, i.e. a string, wire or cable, is connected to the core 48 at one end thereof and extends through the helical spring 50. A hydraulic motor in the form of a cylinder/piston unit 54 is adapted to pull the flexible pulling member 52 to contract the helical spring 50 against an arresting member 56, which is fixed relative to the core 48. A tube 58 hinged to the arresting member 56 extends between the cylinder/piston unit 54 and the arresting member 56, the flexible pulling member 52 running through the tube 58 and being connected to the piston of the cylinder/piston unit 54. FIG. 8 shows a similar embodiment in which a hydraulic transmission conduit 59 is provided between two piston-cylinder assemblies 54, for use as the hydraulic motor/device in FIG. 7.

FIG. 9 shows an embodiment of the invention in which the restriction member comprises two elongated helical springs 60 and 62 having free ends, and a body 64 to which the springs 60,62 are nonrotatably secured at their opposite ends. The body 64 comprises two separate parts secured to opposite end portions of the enclosing elastic hose 8 and is designed with a releasable and lockable joint between the separate parts. An adjustment device in the form of a drive shaft 66 has two opposite end portions connected to the helical springs 60,62, respectively, at their free ends. The coils of the springs 60,62 form left and right hand helices, respectively. A motor 68 is adapted to rotate the drive shaft 66 in one direction to enlarge the coils of the helical springs 60,62 to longitudinally contract the springs 60,62 and to rotate the drive shaft 66 in the opposite direction to reduce the size of the coils of the springs 60,62 to longitudinally extend the springs 60,62. Thus, the elongated helical springs 60,62 defines a restriction opening, the size of which is increased when the springs 60,62 are extended and decreased when the springs 60,62 are contracted.

FIG. 10 shows an embodiment according to the invention which is identical to the embodiment of FIG. 9, except that the adjustment device comprises a gearing having an input shaft 72 and two opposite aligned output shafts 74 and 76 connected to the helical springs 60 and 62, respectively, at their free ends. The input shaft 72 is connected to the output shafts 74,76 such that they rotate at opposite directions upon rotation of the input shaft 72. The coils of the springs 60, 62 form the same helices.

FIGS. 11-14 show an embodiment of the device of the invention in which a hydraulic motor comprises two interconnected cylinders 78 and 80 and two pistons 82 and 84 in the respective cylinders 78,80. The cylinders 78,80 have a common fluid supply inlet member 86, which together with the cylinders 78,80 takes the shape of a Y-pipe. The restriction member comprises an elongated resilient arcuate core 88. The adjustment device comprises two bars 90 and 92 secured to opposite ends of the core 88 and connected to the pistons 82 and 84, respectively. The core 88 defines a restriction opening and is provided with a releasable and lockable joint 94 (FIG. 13) to permit application of the core 88 around the tissue. The core 88 and the cylinders 90,92 are enclosed by a soft elastic hose 96 except at the joint 94 and the inlet member 86. The hose 96 has an outer tubular wall 98 and a central coaxial inner tubular wall 100, which is fixed to the outer wall 98 by spoke members 102 (FIG. 14). The core 88 is loosely fit in the inner tubular wall 100. By supplying fluid to or withdrawing fluid from the inlet 86 the pistons 82 and 84 will move towards or from each other, so that the restriction opening defined by the core 88 is changed by the longitudinal displacement of the bars 90,92.

FIGS. 15-17 show an embodiment of the invention which is identical to the embodiment of FIGS. 11-14, except that the adjustment device comprises an elongated voltage responsive element 104 secured to the opposite ends of the core 88, so that the core 88 and the element 104 form the restriction member. The element 104 is capable of bending inwardly into a bow in response to a voltage applied across the element 104. The radius of curvature of said bow is adjustable by changing the level of the voltage applied to element 104.

Figure 18:
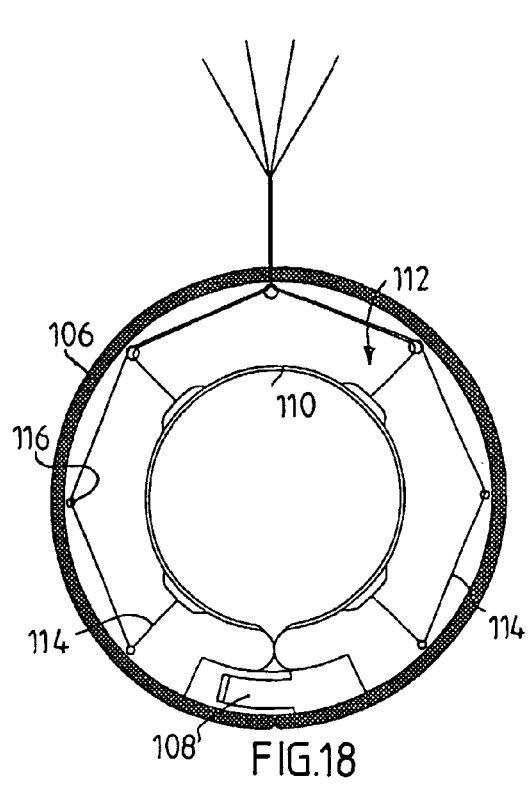

FIG. 18 shows an embodiment of the invention comprising a loop forming means in the form of a substantially rigid outer circular element 106 with a releasable and lockable joint 108. In this embodiment the restriction member comprises an elastic inner circular element 110 formed by the innermost wall portion of an elastic hose 112 extending along the outer element 106. The inner circular element 110 is disposed concentrically within the outer circular element 106. The adjustment device comprises a plurality of threads 114 secured to the elastic inner element 110 along the circumference thereof and running from the inner element 110 via guide members 116 attached to the outer element 106. By pulling all the threads 114 the inner elastic element 110 is pulled under expansion radially outwardly towards the outer element 106.

Figure 19:
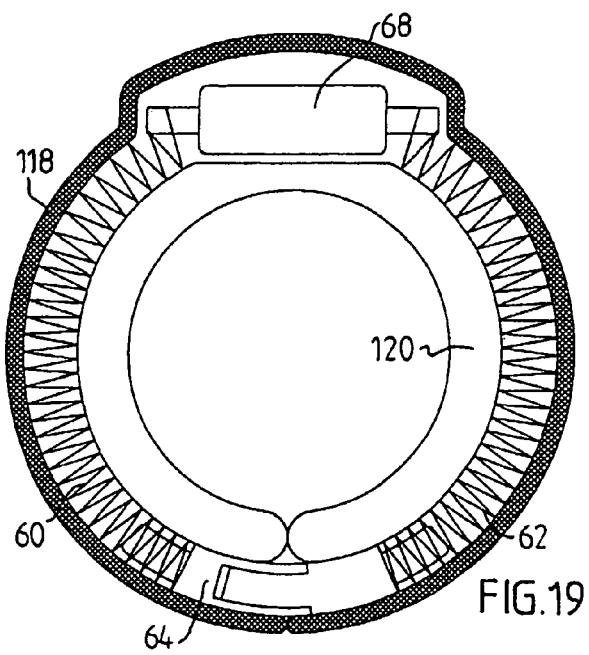

FIG. 19 shows an embodiment which is identical to the embodiment of FIG. 9, except that it comprises a loop forming means in the form of a substantially rigid outer circular element 118 supporting the helical springs 60,62, and a soft elastic inner wall 120 extending along the springs 60,62. When the motor 68 rotates the helical springs 60, 62 in a direction that enlarges the coils of the springs 60,62, the coils are forced by the rigid outer element 118 to expand radially inwardly thereby reducing the size of the restriction opening formed by the circumferential confinement surface of the restriction member (springs 60,62 and body 64).

Figure 20:
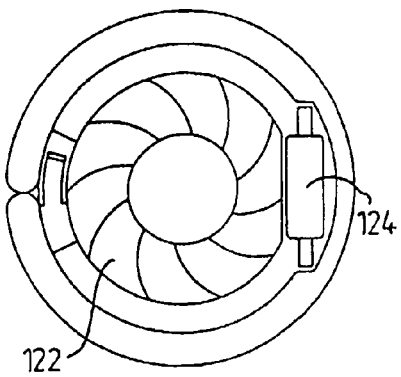

FIG. 20 shows an embodiment of the invention in which a restriction member comprises a plurality of arcuate lamellae 122 arranged like the conventional adjustable aperture mechanism of a camera. The adjustment device, not shown, is conventional and is operated by a motor 124 to adjust the lamellae 122 to change the size of an restriction opening defined by the lamellae 122.

FIGS. 21-23 show an embodiment of the invention in which a restriction member comprises two semi-circular elements 126 and 128 which are hinged together such that the semi-circular elements 126,128 are swingable relative to each other between a fully open state in which they substantially form a circle, illustrated in FIG. 22 and an angular state, in which the size of the restriction opening defined by the semi-circular elements 126,128 is reduced, illustrated in FIG. 23. The adjustment device, not shown, is conventional and is operated by a motor 130 to swing the semi-circular elements 126,128 relative to each other.

FIGS. 24-27 show an embodiment of the invention in which a restriction member comprises an elastic belt 130 forming a circle and having a substantially oval cross-section. The restriction member 130 is provided with a releasable and lockable joint 132. An elastic double walled hose 134 encloses the belt 130 except at the joint 132. The adjustment device, not shown, is conventional and is operated by a motor 136 to turn the belt 130 around the longitudinal extension thereof between a fully open state, in which the inner broader side of the belt 130 forms a substantially cylindrical surface, illustrated in FIG. 26, and a reduced open state, in which the inner broader side of the belt 130 forms a substantially conical surface, illustrated in FIG. 27.

FIG. 28 schematically illustrates a cushion arrangement for protecting the penile tissue, comprising a plurality of cushions 138 disposed in series along a substantially circular holding member 140. This cushion arrangement may be utilized in any of the above described embodiments of the invention.

FIGS. 29A-D provide a block diagram of four different hydraulic transmission configurations. FIG. 29A shows an adjustment device 202, a separate reservoir 204, a one way pump 206 and an alternate valve 208. FIG. 29B shows the adjustment device 202 and an adjustable reservoir 210. FIG. 29C shows the adjustment device 202, a two-way pump 212 and the reservoir 204. FIG. 29D shows a reverse servo system with a first closed system controlling a second system. The servo system comprises an adjustable servo reservoir 210 and a passive adjustable fluid supply reservoir 214. Any of the reservoirs can be the active reservoir, either the servo reservoir 210 or the fluid supply reservoir 214. The reservoir 214 controls a larger adjustable reservoir 216, which is used for the operation of the adjustment device 202 for changing the restriction opening of the restriction member.

Figure 30C:
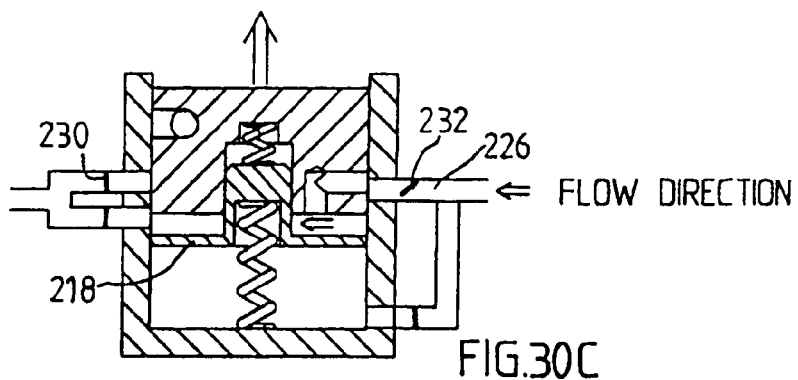
Figure 30D:
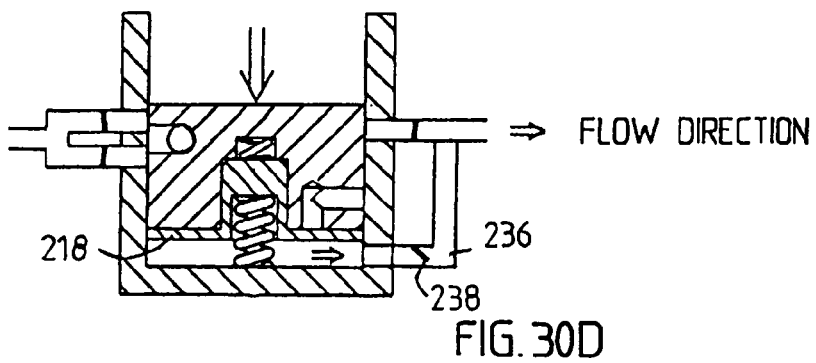

FIGS. 30A-D are cross-sectional views of a pump mechanism adapted to pump fluid in both directions only by mechanically pushing a separate sealing wall portion 218 in one direction. FIG. 30A shows a piston 220 pushed forwards against a spring 222 towards the wall portion 218 and located in a pump housing 224 conducting fluid from a right upper fluid passage 226 of the housing 224 to a left fluid passage 228 of the housing 224. A main valve 230 is open and a nonreturn valve 232 is closed. FIG. 30B illustrates the first pump movement in which the piston 220 has moved forwards and reaches the wall portion 218. FIG. 30C illustrates how the piston 220 moves backwards by the action of the spring 222. The main valve 230 is now closed and the nonreturn valve 232 is open for fluid from the right upper passage 226. FIG. 30D illustrates how the piston 220 is moved further downwards from its position according to FIG. 30B while pushing the wall portion 218 downwards against a second spring 234 that is stronger than spring 222, so that fluid escapes from a right lower fluid passage 236. When moving the piston 220 backwards from the position of FIG. 30D, fluid enters the left fluid passage 228 and a valve 238 in the lower right fluid passage 236 closes.

FIG. 31 is a cross-sectional view of a reservoir 240 defining a chamber 242, the size of which is variable and is controlled by a remote controlled motor 244, in accordance with FIG. 29B or 29D. The reservoir 240 and the motor 244 are placed in a housing 246. The chamber 242 is varied by moving a large wall 248. The wall 248 is secured to a nut 250, which is threaded on a rotatable spindle 252. The spindle 252 is rotated by the motor 244 via an angular gearing, which comprises two conical gear wheels 254 and 256 in mesh with each other. The motor 244 is powered by a battery 258 placed in the housing 246. A signal receiver 260 for controlling the motor 244 is also placed in the housing 246. Alternatively, the battery 258 and the signal receiver 260 may be mounted in a separate place. The signal receiver may comprise any known or conventional device which is capable of receiving a control signal and then operating the motor 244.

FIG. 32 is a cross-sectional view of a reservoir 262 defining a chamber 264, the size of which is variable and is controlled by manual manipulation. A gable wall portion 266 of an open ended inner cylindrical housing 68 is adapted to be pushed downwards to fit in a desired locking groove 270 of a plurality of locking grooves 270 on the mantle wall of the cylindrical housing 268, to reduce the size of the chamber 64. The inner cylindrical housing 268 is suspended by springs 272 and is telescopically applied on an outer cylindrical housing 274. When pushing the inner cylindrical housing 268 it moves downwards relative to the outer cylindrical housing 274 causing the gable wall portion 266 to release from the locking groove 270 and move upwards relative to the inner cylindrical housing 268. When the inner housing 268 is moved upwardly by the action of the springs 272 the size of the chamber 264 is increased.

FIGS. 33A and 33B show a reverse servo means comprising a main ring-shaped fluid reservoir 276 defining a chamber 278, the size of which is variable. Centrally positioned in the main ring-shaped reservoir 276 there is a servo fluid reservoir 280 defining a chamber 282, the size of which is variable. The chamber 282 of the servo reservoir 280 is significantly smaller than the chamber 278 of the main reservoir 276. The two reservoirs 276 and 280 are situated between two opposite separate walls 284 and 286, and are secured thereto. When changing the amount of fluid in the servo reservoir 280, the two opposite walls 284,286 are moved towards or away from each other, whereby the size of the chamber 278 of the main reservoir 276 is changed.

FIG. 34 shows the basic parts of a remote control system of the apparatus of the invention including a motor, for instance the electric motor 22. In this case, the remote control system is based on the transmission of an electromagnetic wave signal, often of a high frequency in the order of 100 kHz-1 gHz, through the skin 330 of the patient. In FIG. 34, all parts placed to the left of the skin 330 are located outside the patient's body and all parts placed to the right of the skin 330 are implanted in the patient's body.

An external signal transmitting antenna 332 is to be positioned close to a signal receiving antenna 334 implanted in the patient's body close to the skin 330. As an alternative, the receiving antenna 334 may be placed for example inside the abdomen of the patient. The receiving antenna 334 comprises a coil, approximately 1-100 mm, preferably 25 mm in diameter, wound with a very thin wire and tuned with a capacitor to a specific high frequency. A small coil is chosen if it is to be implanted under the skin of the patient and a large coil is chosen if it is to be implanted in the abdomen of the patient. The transmitting antenna 332 comprises a coil having about the same size as the coil of the receiving antenna 334 but wound with a thick wire that can handle the larger currents that is necessary. The coil of the transmitting antenna 332 is tuned to the same specific high frequency as the coil of the receiving antenna 334.

An external control unit 336 comprises a microprocessor, a high frequency electromagnetic signal generator and a power amplifier. The microprocessor of the control unit 336 is adapted to switch on/off the generator and to modulate signals generated by the generator to send digital information via the power amplifier and the antennas 332,334 to an implanted control unit 338. To avoid that accidental random high frequency fields trigger control commands, digital signal codes are used. A keypad placed on the external control unit 336 is connected to the microprocessor thereof. The keypad is used to order the microprocessor to send a digital signal to either increase or decrease the size of the restriction opening defined by the loop of the restriction member (e.g. as described above). The microprocessor starts a command by applying a high frequency signal on the antenna 332. After a short time, when the signal has energised the implanted parts of the control system, commands are sent to increase or decrease the size of the restriction opening of the restriction member in predefined steps. The commands are sent as digital packets in the form illustrated below.

| Start pattern, | Command, | Count, | Checksum, |
| 8 bits | 8 bits | 8 bits | 8 bits |

The commands are sent continuously during a rather long time period (e.g. 30 seconds or more). When a new increase or decrease step is desired the Count byte is increased by one to allow the implanted control unit 338 to decode and understand that another step is demanded by the external control unit 336. If any part of the digital packet is erroneous, its content is simply ignored.

Through a line 340, an implanted energiser unit 326 draws energy from the high frequency electromagnetic wave signal received by the receiving antenna 334. The energiser unit 326 stores the energy in a power supply, such as a large capacitor, powers the control unit 338 and powers the electric motor 22 via a line 342.

The control unit 338 comprises a demodulator and a microprocessor. The demodulator demodulates digital signals sent from the external control unit 336. The microprocessor of the control unit 338 receives the digital packet, decodes it and, provided that the power supply of the energiser unit 326 has sufficient energy stored, sends a signal via a signal line 344 to the motor 22 to either increase or decrease the size of the restriction opening of the restriction member depending on the received command code.

Alternatively, the energy stored in the power supply of the energiser unit may only be used for powering a switch, and the energy for powering the motor 22 may be obtained from another implanted power source of relatively high capacity, for example a battery. In this case the switch is adapted to connect the battery to the control unit 338 in an "on" mode when said switch is powered by said power supply and to keep said battery disconnected from the control unit in a "standby" mode when the switch is not powered.

With reference to FIG. 35, the remote control system schematically described above will now be described in accordance with a more detailed embodiment. The external control unit 336 comprises a microprocessor 346, a signal generator 348 and a power amplifier 350 connected thereto. The microprocessor 346 is adapted to switch the signal generator 348 on/off and to modulate signals generated by the signal generator 348 with digital commands that are sent to implanted components of the device of the invention. The power amplifier 350 amplifies the signals and sends them to the external signal transmitting antenna 332. The antenna 332 is connected in parallel with a capacitor 352 to form a resonant circuit tuned to the frequency generated by the signal generator 348.

The implanted signal receiving antenna coil 334 forms together with a capacitor 354 a resonant circuit that is tuned to the same frequency as the transmitting antenna 332. The signal receiving antenna coil 334 induces a current from the received high frequency electromagnetic waves and a rectifying diode 360 rectifies the induced current, which charges a storage capacitor 358. A coil 356 connected between the antenna coil 334 and the diode 360 prevents the capacitor 358 and the diode 360 from loading the circuit of the signal receiving antenna 334 at higher frequencies. Thus, the coil 356 makes it possible to charge the capacitor 358 and to transmit digital information using amplitude modulation.

A capacitor 362 and a resistor 364 connected in parallel and a diode 366 forms a detector used to detect amplitude modulated digital information. A filter circuit is formed by a resistor 368 connected in series with a resistor 370 connected in series with a capacitor 372 connected in series with the resistor 368 via ground, and a capacitor 374, one terminal of which is connected between the resistors 368,370 and the other terminal of which is connected between the diode 366 and the circuit formed by the capacitor 362 and resistor 364. The filter circuit is used to filter out undesired low and high frequencies. The detected and filtered signals are fed to an implanted microprocessor 376 that decodes the digital information and controls the motor 22 via an H-bridge 378 comprising transistors 380, 382, 384 and 386. The motor 22 can be driven in two opposite directions by the H-bridge 378.

The microprocessor 376 also monitors the amount of stored energy in the storage capacitor 358. Before sending signals to activate the motor 22, the microprocessor 376 checks whether the energy stored in the storage capacitor 358 is enough. If the stored energy is not enough to perform the requested operation, the microprocessor 376 waits for the received signals to charge the storage capacitor 358 before activating the motor 22.

FIGS. 36A and 36B show an embodiment of the apparatus of the invention comprising a restriction device 402 having an elongated flexible restriction member 404, such as a belt, a cord or the like. The flexible member 404 extends in a loop around the tissue, suitably an exit vein from the penis. (Alternatively, the flexible member 404 may comprise two separate parts on opposite sides of the vein.) One portion 404A of member 404 is attached to a frame 408 and another portion 404B of member 404 opposite portion 404A in the loop of the flexible member 404 is connected to an adjustment device 410, which is fixed to the frame 408. The adjustment device 410 pulls the flexible member 404 in the direction from portion 404A to squeeze the vein between two opposite lengths of the flexible member 404 to thereby restrict the blood flow in the vein 406, see FIG. 36A, and releases the vein from the flexible member 404 to thereby increase the blood flow in the vein 406, see FIG. 36B.

FIGS. 37A and 37B show an embodiment of the apparatus of the invention comprising a restriction device 412 having two rigid plate or bar elements 414 on opposite sides of the vein 406. An adjustment device 416 moves the rigid elements 412 in parallel towards each other to squeeze the vein 406 between the rigid elements 412 to thereby restrict the blood flow in the vein 406, see FIG. 37A, and moves the rigid elements 412 away from each other to release the vein 406, see FIG. 37B.

FIG. 38 shows an embodiment of the apparatus of the invention comprising a restriction device 418 having two rigid articulated clamping elements 420 positioned on opposite sides of the vein 406. An adjustment device 422 turns the clamping elements 420 toward each other to clamp the vein 406 between the clamping elements 420 to thereby restrict the blood flow in the vein 406, and turns the clamping elements 420 away from each other to release the vein 406 from the clamping elements 420 to thereby increase the blood flow in the vein 406.

FIGS. 39A, 39B and 39C show an embodiment of the apparatus of the invention comprising a restriction device 424 having three bending members in the form of cylindrical rollers 426, 428 and 430 displaced relative one another in a row along the vein 406 and positioned alternately on opposite sides of the vein 406. (Alternatively, each roller 426, 428 and 430 may take the shape of an hour-glass.) An adjustment device 432 moves the two outer rollers 426,430 laterally against the vein 406 in one direction and the intermediate roller 428 against the vein 406 in the opposite direction to bend the vein to thereby restrict the blood flow in the vein 406, see FIG. 39B. To increase or restore the blood flow in the vein 406, the adjustment device 432 moves the rollers 426-430 away from the vein 406 to release the vein from the rollers 426-430, see FIG. 39C.

Figure 40A:
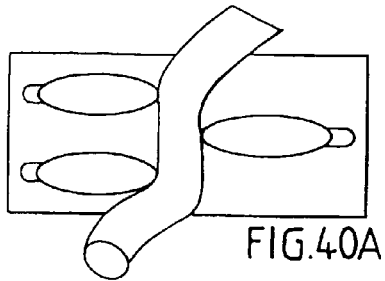
Figure 40B:
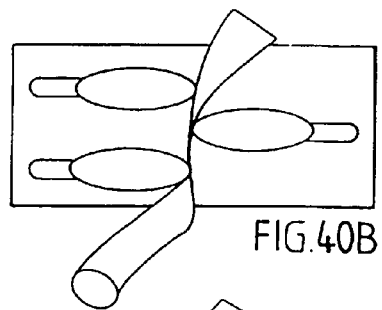
Figure 41A:
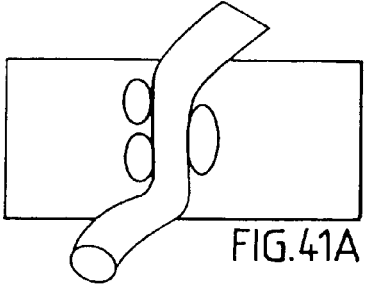
Figure 41B:
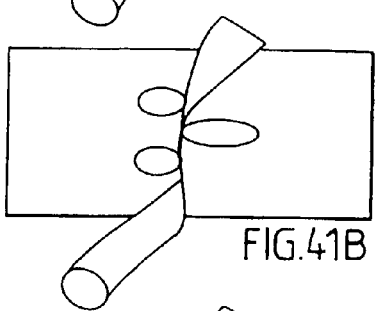
Figure 42A:
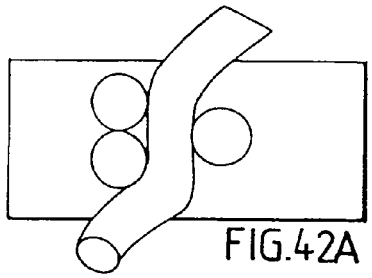
Figure 42B:
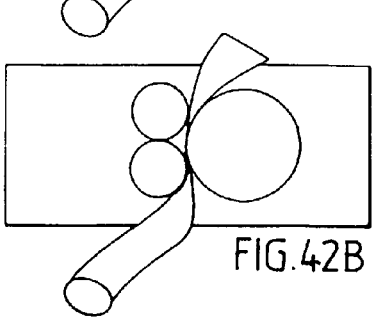
Figure 43A:
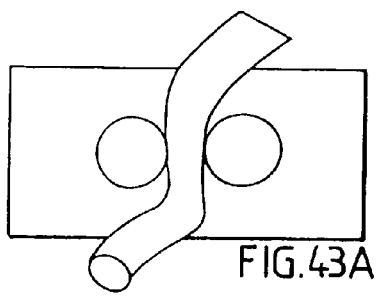
Figure 43B:
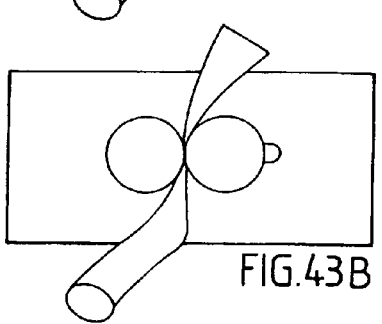
Figure 44A:
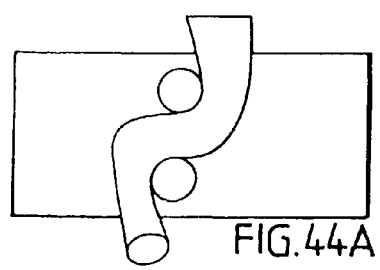
Figure 44B:
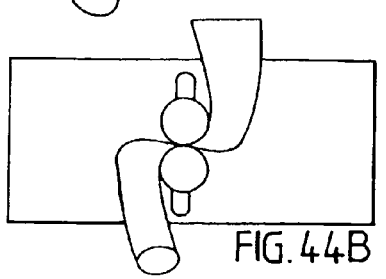

FIGS. 40A through 44B schematically illustrates modifications of the above embodiment according to FIGS. 39A-39C. Thus, FIGS. 40A and 40B show an embodiment similar to that of FIGS. 39A-39C except that the bending members are oval and not rotatable. FIGS. 41A and 41B show an embodiment similar to that of FIGS. 40A and 40B except that the oval bending members are rotatable to release the vein, see FIG. 41A, and squeeze the vein, see FIG. 41B. FIGS. 42A and 42B show an embodiment similar to that of FIGS. 39A-39C except that the intermediate roller has a changeable diameter to release the vein, see FIG. 42A, and squeeze the vein, see FIG. 42B. FIGS. 43A and 43B show an embodiment similar to that of FIGS. 37A-37C except that the rigid elements are replaced by two cylindrical rollers positioned on opposite sides of the vein. Finally, FIGS. 44A and 44B show an embodiment substantially similar to that of FIGS. 43A and 43B except that the restriction device is curved to form an S-shaped curvature of the vein.

FIG. 45 schematically illustrates how any of the above-described embodiments of the male sexual impotence treatment apparatus of the invention may be implanted in a patient. Thus, the apparatus comprises an adjustable restriction device 434 extending around the corpus cavernosum of the patient and a motor operated adjustment device 436 for mechanically adjusting the restriction device 434 to squeeze the corpus cavernosum to thereby restrict the blood flow leaving the penis. The motor, not shown, is integrated in the adjustment device 436 and is reversible to operate the adjustment device 436 to release the corpus cavernosum from the restriction device 434. A wireless remote control of the apparatus comprises an external signal transmitter 438 incorporated in a portable remote-control case and an implanted signal receiver 440, which comprises a control unit for controlling the adjustment device 436 in response to a control signal, for example an electromagnetic wave signal, from the transmitter 438. The signal receiver 440 further comprises an energiser unit which transfers energy from the control signal transmitted by the transmitter 438 into electric energy for energy consuming implanted components of the apparatus, such as the motor for operating the adjustment device 436. The electric energy is conducted via an implanted conductor 442 from the signal receiver 440 to the motor. When the patient wishes to achieve erection, he readily uses the portable remote-control case to activate the implanted adjustment device 436 to temporarily adjust the implanted restriction device 434 to restrict the blood flow leaving his penis.

FIG. 46 shows an embodiment which is identical to the embodiment of FIG. 45, except that the restriction device comprises two restriction members 444 and 446 extending around respective exit veins from the penis. A motor operated adjustment device, not shown, is incorporated in each restriction member 444,446.

There are a number of other conceivable alternative embodiments of the invention that give the same result as the above-described embodiments. For example, the microprocessor of the external and implanted, respectively, control unit may be replaced by discrete components. The power amplifier of the external control unit may be omitted if the signals generated by the signal generator are strong enough. Therefore the invention is to be accorded the broadest interpretation of the appended claims to encompass all equivalent structures and assemblies.

The invention claimed is:

1. A male sexual impotence treatment apparatus, comprising an adjustable restriction device implantable in a male impotent patient for directly engaging a portion of the normal penile tissue or the prolongation thereof of the patient, and an operable adjustment device implantable in the patient for adjusting the restriction device to temporarily contract said portion of the normal penile tissue or the prolongation thereof to restrict the blood flow leaving the penis, when the patient desires to achieve erection, wherein said adjustment device comprises:
   a hydraulic means for operating the adjustment device, comprising:
   (i) a first adjustable reservoir containing hydraulic fluid and being operatively connected to the restriction device,
   (ii) a second adjustable reservoir operatively connected to the first adjustable reservoir such that changes in the amount of fluid in the second adjustable reservoir causes larger changes in the amount of fluid in the first adjustable reservoir, the changes in the amount of fluid in the first reservoir causing corresponding adjustments in the restriction device, and thereby, corresponding changes in restriction of the penile tissue or the prolongation thereof engaged by the restriction device,
   (iii) a third reservoir adapted for subcutaneous implantation, and
   (iv) a hydraulic tube that hydraulically interconnects the second and third reservoirs and that separates the second and third reservoirs from each other,
   wherein the third reservoir is adjustable to change the amount of fluid therein to cause fluid flow in the hydraulic tube and a change of amount of fluid in the second reservoir, and wherein the third reservoir is smaller than the first reservoir.

2. An apparatus according to claim 1, wherein the restriction device is operable to contract said portion of the patient's penile tissue or the prolongation thereof, when the patient desires to achieve erection, such that the penile arterial blood flow is at least substantially unrestricted, whereas the penile venous blood flow is substantially restricted.

3. An apparatus according to claim 1, wherein the restriction device is designed for engagement with both of the corpora cavernosa or crura of the penis or the prolongations thereof as a single unit, or for engagement with each of the two corpora cavernosa or crura or the prolongation thereof as two separate units.

4. An apparatus according to claim 3, wherein the restriction device is adapted to control the cross-sectional area of a blood flow passageway formed by the patient's penile exit veins or corpora/crura cavernosa.

5. An apparatus according to claim 4, wherein the restriction device is operable to open and close the blood flow passageway.

6. An apparatus according to claim 5, wherein the restriction device is adapted to steplessly control the cross-sectional area of the blood flow passageway.

7. An apparatus according to claim 1, wherein said portion of the penile tissue comprises one or more of the exit veins from the penis.

8. An apparatus according to claim 1, wherein the adjustment device is adapted to adjust the restriction device in a non-magnetic or non-thermal manner.

9. An apparatus according to claim 1, wherein the adjustment device is powered.

10. An apparatus according to claim 1, wherein the restriction device is non-inflatable.

11. An apparatus according to claim 1, wherein the restriction device comprises an element to be placed on one side of said portion of the penile tissue, and the adjustment device is adapted to squeeze said portion of the penile tissue between the element and the human bone or tissue to decrease the blood flow leaving the penis.

12. An apparatus according to claim 1, wherein the restriction device comprises at least one elongated restriction member and forming means for forming the restriction member into at least a substantially closed loop around said portion of the penile tissue, the loop defining a restriction opening, whereby the adjustment device is adapted to adjust the restriction member in the loop to change the size of the restriction opening.

13. An apparatus according to claim 12, wherein the restriction device comprises several elongated restriction members to be formed into at least substantially closed loops around the penile tissue.

14. An apparatus according to claim 12, wherein, the adjustment device is adapted to adjust the longitudinal extension of the elongated restriction member in said loop to change the size of the restriction opening.

15. An apparatus according to claim 12, wherein the restriction member forms a radial innermost circumferential confinement surface in said loop of the restriction member, and the adjustment device is adapted to mechanically adjust the restriction member such that at least a portion of the confinement surface is substantially radially displaced in said loop.

16. An apparatus according to claim 15, wherein the restriction member comprises an elastic annular element forming the confinement surface, and the adjustment device is adapted to change the diameter of the elastic annular element.

17. An apparatus according to claim 12, wherein the forming means is adapted to form the restriction member into a loop having a predetermined size or a size selected from several predetermined sizes.

18. An apparatus according to claim 12, wherein the adjustment device is adapted to change the size of the restriction opening such that the outer circumferential confinement surface of the restriction member is changed.

19. An apparatus according to claim 12, wherein the adjustment device is adapted to change the size of the restriction opening such that the outer circumferential confinement surface of the restriction member is unchanged.

20. An apparatus according to claim 1, wherein the restriction device comprises at least two elements to be placed on different sides of said portion of the penile tissue, and the adjustment device is adapted to squeeze said portion of the penile tissue between the elements to restrict the blood flow leaving the penis, and to release said portion of the penile tissue from the elements to increase the blood flow leaving the penis.

21. An apparatus according to claim 1, wherein the restriction device comprises at least two articulated clamping elements to be positioned on opposite or different sides of said portion of the penile tissue, and the adjustment device is adapted to turn the clamping elements toward each other to clamp said portion of the penile tissue between the clamping elements to restrict the blood flow leaving the penis, and to turn the clamping elements away from each other to release said portion of the penile tissue from the clamping elements to increase the blood flow leaving the penis.

22. An apparatus according to claim 1, wherein the restriction device is adapted to bend a portion of said portion of the penile tissue.

23. An apparatus according to claim 22, wherein the restriction device comprises at least two bending members to be positioned on opposite or different sides of said portion of the penile tissue and to be displaced relative to each other along the penile tissue, and the adjustment device is adapted to move the bending members against said portion of the penile tissue to bend it to restrict the blood flow leaving the penis, and to move the bending members away from said portion of the penile tissue to release it from the bending members to increase the blood flow leaving the penis.

24. An apparatus according to claim 23, wherein the bending members comprise rollers.

25. An apparatus according to claim 1, wherein the restriction device is adapted to rotate a portion of the penile tissue.

26. An apparatus according to claim 1, further comprising an operation device for transporting fluid between the third and the second reservoirs.

27. An apparatus according to claim 26, wherein the operation device comprises a pump.

28. An apparatus according to claim 26, wherein the operation device is manually operated.

29. An apparatus according to claim 26, wherein the operation device comprises a motor, preferably an electric motor.

30. An apparatus according to claim 29, wherein the motor is reversible.

31. An apparatus according to claim 29, comprising an implantable reversing device for reversing the motor.

32. An apparatus according to claim 26, wherein the operation device is adapted to operate the adjustment device by using the hydraulic fluid of the first reservoir.

33. An apparatus according to claim 32, wherein the first reservoir contains a predetermined amount of hydraulic fluid.

34. An apparatus according to claim 33, wherein the first reservoir comprises first and second wall portions and is adapted to provide relative displacement between the first and second wall portions of the first reservoir, in order to change the volume of the first reservoir.

35. An apparatus according to claim 34, wherein said relative displacement is performed in response to the pressure in the reservoir.

36. An apparatus according to claim 35, further comprising an alarm adapted to generate an alarm signal in response to the lapse of a predetermined time period during which pressure controlling in the third reservoir exceeds a predetermined high value.

37. An apparatus according to claim 26, wherein the operation device comprises magnetic means, electric means or manual manipulation means or a combination thereof.

38. An apparatus according to claim 1, wherein the hydraulic means is devoid of any non-return valve.

39. An apparatus according claim 1, wherein the second reservoir defines a chamber containing servo fluid, and comprises first and second wall portions of the second reservoir, which are displaceable relative to each other to change the volume of the chamber of the second reservoir.

40. An apparatus according to claim 39, wherein the third reservoir defines a chamber for a further predetermined amount of fluid and the hydraulic operation device is adapted to change the volume of the chamber and thereby control the amount of fluid in the second reservoir.

41. An apparatus according to claim 40, wherein the third reservoir comprises first and second wall portions, which are displaceable relative to each other to change the volume of the chamber of the third reservoir.

42. An apparatus according to claim 41, wherein the third reservoir increases the amount of fluid in the second reservoir in response to a predetermined first displacement of the first wall portion of the third reservoir relative to the second wall portion of the third reservoir and decreases the amount of fluid in the second reservoir in response to a predetermined second displacement of the first wall portion of the fluid third reservoir to the second wall portion of the third reservoir.

43. An apparatus according to claim 1, wherein the hydraulic means comprises a first reservoir implantable in the patient and containing a predetermined amount of hydraulic fluid, and a conduit providing fluid connection between the first reservoir and the restriction device, and operates by distributing hydraulic fluid through the conduit between the first reservoir and the restriction device, the conduit and restriction adjustment device being devoid of any non-return valve to permit free flow of hydraulic fluid in both directions in the conduit.

44. An apparatus according to claim 43, wherein the first reservoir forms a fluid chamber with a variable volume, and the adjustment device is adapted to distribute fluid from the chamber to the restriction device by reduction of the volume of the chamber and to withdraw fluid from the restriction device by expansion of the volume of the chamber.

45. An apparatus according to claim 1, further comprising an injection port subcutaneously implantable in the patient and in fluid communication with the third reservoir.

46. An apparatus according to claim 45, wherein the injection port is integrated in the third reservoir.

47. An apparatus according claim 1, further comprising a wireless remote control for non-invasively controlling the adjustment device.

48. An apparatus according to claim 47, wherein the remote control comprises a separate signal transmitter and/or receiver and an implantable signal receiver and/or transmitter, for transmitting and/or receiving a control signal.

49. An apparatus according to claim 48, wherein the signal receiver comprises a control unit adapted to control the adjustment device in response to the control signal.

50. An apparatus according to claim 49, further comprising an implantable energiser unit for providing energy to energy consuming components of the apparatus to be implanted in the patient.

51. An apparatus according to claim 50, comprising an operation device for operating the hydraulic means, wherein said operation device comprises an implantable motor or pump.

52. An apparatus according to claim 51, wherein the control unit is adapted to control the energiser unit to power the motor or pump with energy in response to the control signal.

53. An apparatus according to claim 51, wherein the motor is an electric motor.

54. An apparatus according to claim 53, comprising a wireless energy transmitter, wherein the energiser unit comprises an energy transfer means adapted to transform energy from the wireless energy into electric energy.

55. An apparatus according to claim 54, wherein the energiser unit is adapted to transform energy from the wireless energy into a direct or alternating current.

56. An apparatus according to claim 54, wherein the energiser unit comprises a rechargeable electric power supply for storing the electric energy and the control unit is adapted to power the electric motor with energy from the rechargeable electric power supply in response to the control signal.

57. An apparatus according to claim 54, wherein the energy transfer means is adapted to directly power the motor or pump with transferred energy.

58. An apparatus according to claim 57, wherein the energy transfer means is adapted to transfer wireless energy in the form of electromagnetic waves excluding radio waves.

59. An apparatus according to claim 57, wherein the energy transferred by the energy transfer means comprises an electric field or a magnetic field.

60. An apparatus according to claim 59, wherein the signal comprises a wave signal.

61. An apparatus according to claim 60, wherein the wave signal comprises an electromagnetic wave signal, a sound wave signal or a carrier wave signal.

62. An apparatus according to claim 61, wherein the carrier signal is frequency, amplitude or frequency and amplitude modulated.

63. An apparatus according to claim 61, wherein the control signal comprises a wave signal comprising one of a sound wave signal including an ultrasound wave signal, an electromagnetic wave signal including an infrared light signal, a visible light signal, an ultra violet light signal and a laser light signal, a micro wave signal, a radio wave signal, an x-ray radiation signal, and a gamma radiation signal.

64. An apparatus according to claim 57, wherein the energy transferred by the energy transfer means comprises a signal.

65. An apparatus according to claim 64, wherein the signal comprises analog or digital pulses.

66. An apparatus according to claim 65, wherein the analog or digital pulses comprise a magnetic field or an electric field.

67. An apparatus according to claim 50, wherein the energiser unit (comprises a battery, an electrically operable switch adapted to connect the battery to the signal receiver in an "on" mode when the switch is powered and to keep the battery disconnected from the signal receiver in a "standby" mode when the switch is not powered, and a rechargeable electric power supply for powering the switch.

68. An apparatus according to claim 67, wherein the control unit is adapted to power the electric motor or pump with energy from the battery in response to a control signal received from the signal transmitter, when the switch is in its "on" mode.

69. An apparatus according to claim 50, further comprising an external energy transmitter for transmitting wireless energy, wherein the energiser unit comprises a battery and a switch operable by the wireless energy transmitted by the external transmitter, for connecting the battery to the signal receiver in an "on" mode when the switch is powered by the wireless energy and to keep the battery disconnected from the signal receiver in a "standby" mode when the switch is not powered.

70. An apparatus according to claim 50, wherein the energiser unit comprising an energy transfer means, wherein said energy transfer means is adapted to transform energy from the control signal, as it is transmitted to the signal receiver into electric energy.

71. An apparatus according to claim 47, wherein the remote control is capable of obtaining information from implantable components of the apparatus and of commanding the adjustment device to adjust the restriction device in response to obtained information.

72. An apparatus according to claim 1, further comprising an implantable energiser unit for providing energy to energy consuming components of the apparatus to be implanted in the patient.

73. An apparatus according to claim 72, further comprising an external energy transmitter for transmitting wireless energy, wherein the energiser unit is adapted to transform the wireless energy into electric energy.

74. An apparatus according to claim 73, comprising an operation device for operating the hydraulic means, said operation device comprising an electric motor or pump, wherein the energiser unit is adapted to power the electric motor or pump with the electric energy transformed from the wireless energy.

75. An apparatus according to claim 72, further comprising an external energy transmitter for transmitting wireless energy, wherein the energiser unit comprises a battery and a switch operable by the wireless energy transmitted by the external transmitter, for connecting the battery to the implantable energy consuming components of the apparatus in an "on" mode when the switch is powered by the wireless energy and to keep the battery disconnected from the energy consuming components in a "standby" mode when the switch is not powered.

76. An apparatus according to claim 75, wherein the external energy transmitter is adapted to directly power the switch with the wireless energy to switch into the "on" mode.

77. An apparatus according to claim 1, further comprising implantable electrical components including at least one voltage level guard.

78. An apparatus according to claim 77, wherein the electrical components are devoid of any current detector and/or charge level detector.

79. An apparatus according to claim 77, further comprising an implantable capacitor or accumulator, wherein the charge or discharge of the capacitor or accumulator is controlled by use of the voltage level guard.

80. An apparatus according to claim 1, further comprising implantable electrical components including a single voltage level guard.

81. An apparatus according to claim 1, further comprising a wireless energy transmitter and an energy transfer means for wireless transfer of wireless energy from outside the patient's body to the adjustment device and/or other energy consuming implantable components of the apparatus.

82. An apparatus according to claim 81, wherein wireless energy transmitter is adapted to intermittently transfer the energy in the form of a train of energy pulses and wherein the energy transfer means transfers the wireless energy into electric energy for direct use in connection with the energising of the energy consuming components of the apparatus.

83. An apparatus according to claim 82, wherein the energy transfer means is adapted to transfer electric energy to a train of electric pulses, and further comprising an implantable capacitor for producing the train of energy pulses.

84. An apparatus according to claim 83, wherein the capacitor has a capacity less than 0.1 F.

85. An apparatus according to claim 81, wherein the energy transfer means is adapted to transfer magnetic energy, non-magnetic energy, electromagnetic energy, non-electromagnetic energy, kinetic energy, non-kinetic energy, sonic energy, non-sonic energy, thermal energy or non-thermal energy.

86. An apparatus according to claim 81, comprising an energiser unit, wherein the transferred energy are stored in the energiser unit for later use for any of the energy consuming implantable components of the apparatus.

87. An apparatus according to claim 86, wherein the energiser unit (326), comprises a rechargeable battery or accumulator for supplying energy to any of the energy consuming implantable components of the apparatus.

88. An apparatus according to claim 1, comprising:
an operation device for operating the hydraulic means, said operation device comprising a motor or a pump; and
an energy transmission device adapted to transmit wireless energy in the form of a magnetic field or electromagnetic waves for direct power of the motor or pump, as the wireless energy is being transmitted.

89. An apparatus according to claim 88, wherein the pump is not a plunger type of pump.

90. An apparatus according to claim 1, further comprising a pressure sensor for directly or indirectly sensing the pressure against the restriction device.

91. An apparatus according to claim 90, wherein the restriction device is controlled in response to signals from the pressure sensor.

92. An apparatus according to claim 1, comprising a wireless energy transmitter and further comprising an implantable energy transfer means for transferring wireless energy directly or indirectly into energy different than the wireless energy for operation of the restriction device.

93. An apparatus according to claim 92, wherein the energy transfer means transforms the wireless energy into kinetic energy for operation of the restriction device.

94. An apparatus according to claim 93, wherein the energy transfer means transforms the wireless energy in the form of sound waves into electric energy for operation of the restriction device.

95. An apparatus according to claim 1, further comprising an implantable reversing device, wherein the restriction device is capable of performing a reversible function and the reversing device reverses the reversible function.

96. An apparatus according to claim 1, further comprising an implantable accumulator or battery and means for controlling the accumulator or battery from outside the patient's body to supply energy to the adjustment device and/or other implantable energy consuming components of the apparatus.

97. An apparatus according to claim 1, wherein the adjustment device is adapted to adjust the restriction device in a non-manual manner.

98. An apparatus according to claim 1, wherein the restriction device is designed for implantation in the base of the patient's penis or its prolongation.

99. An apparatus according to claim 1, further comprising an adjustment device for adjusting the restriction device to change the restriction of the blood flow passageway, wherein the adjustment device is adapted to mechanically adjust the restriction device, or adapted to hydraulically adjust the restriction device by using hydraulic means which is devoid of hydraulic fluid of the kind having a viscosity that substantially increases when exposed to heat or a magnetic field.

100. An apparatus according to claim 99, comprising an energy transforming device adapted to transform wireless energy in the form of sound waves directly into electric energy.

101. An apparatus according to claim 100, wherein the energy transforming means comprises a capacitor.

102. An apparatus according to claim 101, wherein the capacitor is adapted to produce electric pulses from the transformed electric energy.

* * * * *